US008569335B2

(12) United States Patent
Vizioli et al.

(10) Patent No.: US 8,569,335 B2
(45) Date of Patent: Oct. 29, 2013

(54) COMPOUNDS DERIVED FROM TAURINE, PROCESS OF THEIR PREPARATION AND PHARMACEUTICAL COMPOSITIONS CONTAINING THESE

(75) Inventors: Ednir D. Vizioli, Araraquara (BR); Chung M. Chin, Araraquara (BR); Renato F. Menegon, Araraquara (BR); Lorena Blau, Araraquara (BR); Jean L. Santos, Araraquara (BR); Maria D. Longo, Araraquara (BR)

(73) Assignees: EMS S.A., Hortolandia-SP (BR); Universidade Estadual Paulista Julio de Mesquinta Filho—UNESP, Sao Paulo-SP (BR)

( * ) Notice: Subject to any disclaimer, the term of this patent is extended or adjusted under 35 U.S.C. 154(b) by 307 days.

(21) Appl. No.: 12/937,188

(22) PCT Filed: Apr. 9, 2009

(86) PCT No.: PCT/BR2009/000097
§ 371 (c)(1),
(2), (4) Date: Dec. 3, 2010

(87) PCT Pub. No.: WO2009/124371
PCT Pub. Date: Oct. 15, 2009

(65) Prior Publication Data
US 2011/0118303 A1    May 19, 2011

(30) Foreign Application Priority Data
Apr. 9, 2008 (BR) ...................... 0800951

(51) Int. Cl.
*A61K 31/095* (2006.01)
(52) U.S. Cl.
USPC ........... 514/301; 514/245; 514/430; 514/449; 514/465; 514/708
(58) Field of Classification Search
USPC ................. 514/301, 245, 430, 449, 465, 708; 562/44; 564/500
See application file for complete search history.

(56) References Cited

U.S. PATENT DOCUMENTS

| 4,259,332 A | 3/1981 | Passoni et al. |
| 5,326,907 A * | 7/1994 | Partis et al. .................. 562/44 |
| 2006/0211705 A1 | 9/2006 | Arora et al. |

FOREIGN PATENT DOCUMENTS

CN    1098091 A    2/1995

OTHER PUBLICATIONS

Olsen et al; Drug Metabolism and Disposition, 35(5), 2007, 758-764.*
Olsen et al; Chemical Research in Toxicology, 2005, 18 (11), 1729-1736.*
Olsen et al; Xenobiotica, 2003, 33(5), 561-570.*
Mano et al; Journal of Chromatography B, 776, 2002, 125-131.*
Shirley et al; Journal of Pharmacolgy and Experimental Therapeutics, 1994, 269 (3), 1166-1175.*
Mori et al; Drug Metabolism and Disposition, 1985, 13 (2), 239-45.*
Turnbull et al; Journal of Medicinal Chemistry, 1974, 17 (1) 45-48.*
Rodriguez-Spong et al ; Advanced Drug Delivery Reviews 2004, 56, 241-274.*
Stierlin et al ; Xenobiotica, 1979, 10 (9) 601-610.*
Bradbury et al; Xenobiotica, 1981, 11 (10) 665-674.*
Olsen, Jorgen et al. "In Vitro and in Vivo Studies on Acyl-Coenzyme A-Dependent Bioactivation of Zomepirac in Rats" Chemical Research in Toxicology (2005), 18(11).1729-1736 (abstract). CAPLUS [online] Copyright 2009 ACS on STN [retrieved on Nov. 26, 2009 ]. Retrieved from: TN International. Karlsruhe. Accession No. 2005: 1118084 CAPLUS.
Olsen, J. et at "Identification of coenzyme A-related tolrnetin metabolites in rats: relationship with reactive drug metabolites" Xenobiotica (2003). 33(5). 561-570 (abstract). CAPLUS [online] Copyright 2009 ACS on STN [retrieved on Nov. 26, 2009 ]. Retrieved from: STN International, Karlsruhe. Accession No. 2003:389763 CAPLUS.
Mano, Nariyasu et al. "Rapid and simple quantitative assay method for diastereomeric flurbiprofen glucuronides in the incubation mixture" Journal of Chromatography, B: Analytical Technologies in the Biomedical and Life Sciences (2002). 776(1), 125-131 (abstract). CAPLUS [online] Copyright 2009 ACS on STN [retrieved on Nov. 26, 2009]. Retrieved from: STN International, Karlsruhe. Accession No. 2002:695184 CAPLUS.

(Continued)

Primary Examiner — Johann R Richter
Assistant Examiner — Pancham Bakshi
(74) Attorney, Agent, or Firm — Arent Fox LLP

(57) ABSTRACT

The present invention relates to compounds derived from taurine with non-steroidal anti inflammatory activity.
In a first embodiment, the present invention relates to compounds derived from taurine, in which taurine is bound directly by means of an amide bond or through an spacing group, to a compound selected from the group of non-steroidal anti inflammatory compounds, cited as derived from taurine presenting the Formula (I):

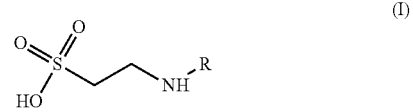

(I)

in which R means the component with non-steroidal anti inflammatory activity.
In a second embodiment, the invention provides a process for obtaining the compounds of Formula (I) by reaction of taurine with a compound belonging to the group of non-steroidal anti inflammatory (NSAIs), in order to obtain a compound derived from taurine by direct bond or through a spacing group of the taurine to the NSAI.
The invention also relates to the pharmaceutical compositions comprising at least one compound derived from taurine presenting non-steroidal anti inflammatory activity.

3 Claims, 4 Drawing Sheets

(56) References Cited

OTHER PUBLICATIONS

Morl, Yukio et al. "Species differences in the metabolism of suprofen in laboratory animals and man" Drug Metabolism and Disposition (1985), 13(2),239-45 (abstract). CAPLUS [online] Copyright 2009 ACS on STN [retrieved on Nov. 26, 2009]. Retrieved from: STN International, Karlsruhe. Accession No. 1985:400118 CAPLUS.

Bradbury. A. et al. "The enhanced biliary secretion of a taurine conjugate in the rat after intraduodenal administration of high doses offenclozic acid" Xenobiotica (1981), 11(10),665-74 (abstract). CAPLUS [online] Copyright 2009 ACS on STN [retrieved on Nov. 26, 2009]. Retrieved from: STN International. Karlsruhe. Accession No. 1982:210333 CAPLUS.

Turnbull, Lennox B. et al. "Disposition and Metabolism of 4- 1-3, 14, 15 methyl-2-(4-phenylbenzyl)-2-oxazoline-4-methanol in the rat and dog" Journal of Medicinal Chemistry (1974), 17(1),45-8 (abstract). CAPLUS [online] Copyright 2009 ACS on STN [retrieved on Nov. 26, 2009]. Retrieved from: STN International, Karlsruhe. Accession No. 1974:103751 CAPLUS.

* cited by examiner

COMPOUNDS DERIVED FROM TAURINE, PROCESS OF THEIR PREPARATION AND PHARMACEUTICAL COMPOSITIONS CONTAINING THESE

CROSS-REFERENCE TO RELATED APPLICATION

This application is a National Stage entry of International Application No. PCT/BR2009/000097, filed Apr. 9, 2009, which claims priority to Brazilian Application No. PI0800951-1, filed Apr. 9, 2008, the disclosure of the prior application is hereby incorporated in its entirety by reference.

FIELD OF THE INVENTION

The present invention relates to novel drugs derived from taurine, preferentially for use as non-steroidal anti inflammatory (NSAI) adjuvants, the obtaintion of such novel drugs and their use in pharmaceutical compositions for treatment of medical conditions including inflammatory processes, rheumatoid arthritis, ulcerative colitis, Chron's disease, and their use as antipyretics, analgesics and platelet anti aggregants.

BACKGROUND OF THE INVENTION

The inflammatory processes have always received great attention in science for being the first biological sign in any abnormality state of a medical condition.

Inflammation is fundamentally a protection response triggered by physical, chemical and biological stimulus that may lead to disturbances that can culminate in tissue necrosis.

In the '70s, after Vane and colleagues (see Vane, J. R. (1971). "Inhibition of prostaglandin synthesis as a mechanism of action for aspirin-like drugs". *Nature-New Biology* 231(25):232-5) demonstrated the participation of prostaglandins as mediators of inflammation, through its inhibition by acetyl salicylic acid, the research have intensified with the development of uncountable families of anti inflammatory drugs, especially the ones known as non-steroidal anti inflammatory (NSAI) drugs (see ROBERTS, L. J.; MORROW, J. D. "Analgesic-antipyretic and antiinflamatory agents and drugs employed in the treatment of gout". In: HARMAN, J. G.; LIMBIRD, L. E. (Eds.). Goodman & Gilman's: the pharmacological bases of therapeutics. New York: MacGraw-Hill, 2001, p. 687-732).

The NSAIs are drugs largely used, constituting an important medicamental resource in despite of the possibility of causing serious side effects, such as gastric irritations (high incidence) and hypertension, causing also liver, kidney, spleen, blood and bone marrow damages (see RANG, H. P.; DALE, M. M.; RITTER, J. M. Farmacologia. Fourth ed. Rio de Janeiro: Guanabara Koogan, 2001, p. 692).

The mechanism of action for NSAI drugs encompasses the inhibition of cyclooxygenases (COX), denominated COX-1 (constitutive form and its inducible form COX-2), interfering in the synthesis of prostaglandins (PG) and reducing the inflammatory reactions.

The prostaglandins perform important physiological functions; among them is gastrintestinal cytoprotection and vascular homeostasis.

COX-1 is responsible for the synthesis of cytoprotector prostaglandins of the gastrintestinal tract and for the synthesis of tromboxans that participate in the formation of platelets aggregation (see Allison, Howatson, Torrence, Lee and Russell. "Gastrointestinal Damage Associated with the Use of Nonsteroidal Antiinflammatory Drugs". *N. Engl. J. Med.* (1992) Vol. 327, pp. 749-754). Regarding COX-2, it is known that it is characterized for presenting a short life, and its production occurs from stimulus in response to endotoxins and cytotoxins. It is important to highlight the fact that COX-2 inhibits the prostaglandins responsible for biosynthesis in inflammatory cells (monocytes and macrophages) as well as in the central nervous system (see Masferrer, Zweifel, Manning, Hauser, Leahy, Smith, Isakson and Seibert, "Selective Inhibition of Inducible Cyclooxygenase-2 in vivo is Antiinflammatory and Nonulcerogenic", *Proc. Natl. Acad. Sci. U.S.A.* (1994) Vol. 91, pp. 3228-3232; Vane, Mitchell, Appleton, Tomlinson, Bishop-Bailey, Croxtall and Willoughby, "Inducible Isoforms of Cyclooxygenase and Nitric Oxide Synthase in Inflammation", *Proc. Natl. Acad. Sci. U.S.A.* (1994) Vol. 91, pp. 2046-2050; Harada, Hatanaka, Saito, Majima, Ogino, Kawamura, Ohno, Yang, Katori and Yamamoto, "Detection of Inducible Protaglandin H Synthase-2 in Cells in the Exudate of Rat Carrageenin-Induced Pleurisy", *Biomed. Res.* (1994) Vol. 15, pp. 127-130; Katori, Harada, Hatanaka, Kawamura, Ohno, Aizawa and Yamamoto, "Induction of Prostaglandin H Synthase-2 in Rat Carrageenin-Induced Pleurisy and Effect of a Selective COX-2 Inhibition", *Advances in Prostaglandin, Thromboxana, and Leukotriene Research* (1995) Vo. 23, pp. 345-347; and Kennedy, Chan, Culp and Cromlish, "Cloning and Expression of Rat Prostaglandin Endoperoxide Synthase (Cyclooxigenase-2) cDNA", *Biochem. Biophys. Res. Commun.* (1994) Vol. 197, pp. 494-500).

The traditional NSAI drugs such as ASA (acetyl salicylic acid), diclophenac, ibuprophen, and naproxen inhibit COX-1 and COX-2. This non-selectivity of NSAI drugs leads also to the inhibition of prostaglandins, which are important for participating in gastric protection.

In order to reduce side effects caused by traditional NSAI drugs, an enormous quantity of COX-2 selective drugs (COX-2 inhibitors) have been researched, some of which are available in the market.

There are evidences that the reduction of the gastrintestinal side effects caused by COX-2 selective inhibitors leads to an adaptative response to the gastric damage, which does not occur when using COX-1 inhibitors (see PESKAR, B. M.; EHRLICH, K.; PESKAR, B. A. "Interaction of cyclooxigenase-2 inhibitor and salicylate in gastric mucosal damage", European Journal of Pharmacology, v. 434, n. 1-2, p. 65-70, 2002; YAMAMOTO, H. et al. "Inducible types of cyclooxigenase and nitric oxide synthase in adaptive cytoprotection in rat stomachs", Journal of Physiology, v. 93, p. 405-12, 1999).

On the other hand, there are no studies that demonstrate the differences in efficacy among the COX-2 selective inhibitors, even though there is proof of the reduction of the adverse gastrintestinal effects caused by them. The problem with these inhibitors appears when it is taken into consideration the adverse cardiovascular effects reported by Stacy et al. (see STACY, Z. A.; DOBESH, P. P.; TRUJILLO, T. C. "Cardiovascular risks of cyclooxygenase inhibition", Pharmacotherapy, v. 26, n. 7, p. 919-938, 2006), being, for this reason, preferred the use of non-selective anti inflammatory drugs.

In fact, the safety of known COX-2 inhibitors have been questioned. The most famous event occurred with the "blockbuster" rofecoxib, with commercial name of Vioxx®, produced by Merck laboratories, which was removed from the market in 2004 after clinical researches demonstrated that it caused a higher risk of heart attack and brain stroke. Other three COX-2 inhibitors that are available in the Brazilian market, celecoxib (Celebra®), valdecoxib (Bextra®) and etoricoxib (ARCOXIA®) are under intense clinical studies in order to verify the safety of their use. In addition, in Apr. 5, 2005, FDA (Food and Drug Administration) has suspended the commercialization of Bextra in the United States and also, in May, 2007, it did not approve the commercialization of Arcoxia.

For all these reasons, the NSAI drugs are still the ones largely used as an important medicamental resource, in spite of the possibility of causing serious known side effects (principally gastric ulceration).

It is still worth mention the role of nitric oxide in the inflammatory processes. In fact, nitric oxide (NO) began to received attention by physiologists with the discovery, in 1986, of Ignaro and collaborators that have described its function as a endothelium derived relaxation factor (EDRF) and have proposed the participation of nitric oxide in the processes of pro inflammatory actions with effects in the vasodilatation and of stimulus of prostaglandins production, as well as anti inflammatory action in order inhibit neutrophyls and platelets, being, therefore, dependent of an immuno-regulated factor (see MONCADA, PALMER, & HIGGS, "The discovery of nitric oxide as the endogenous nitrovasodilator", *Hypertension*, v. 12, p. 365-372, 1988).

The nitric oxide is a colorless gas, paramagnetic, water soluble in the proportion of 2-3 moles per $dm^3$ and presents a boiling point around $-141.7°$ C. It is produced in vivo through interaction, catalyzed by enzymes (nitric oxide synthase—NOS), with molecular oxygen and L-arginine (as substrate). Nitric oxide becomes a free radical that, differently from many other free radicals, does not dimerize in the gaseous phase at room temperature and pressure, even though in the liquid state it may form $N_2O_2$. When the loss of an electron of the nitric oxide free radical occurs leads to the formation of the nitrosil ion ($NO^+$).

Among the evident chemical properties of nitric oxide, it can be highlighted the possibility of radical formation and, consequently, its biological participation as electrophile, oxidant agent, salt and complex formation agent. In the biological system, the radical form of nitric oxide is associated to other species of nitrogen compounds, such as nitrite ($NO_2$), nitrate ($NO_3$) and peroxynitrite ($NO_4$).

The constitutive isoforms of nitric oxide (cNOS) are subdivided in neuronal (nNOS) and endothelial (eNOS) and, depending in which tissue they are found, they are calcium dependent and can be activated by the calcium binding protein (calmodulin-CaM), through agonists such as acetylcholine (ACh), adenine diphosphate (ADP), bradicinine (Bk) and glutamate (see BARRETO, R. L.; CORREIA, C. R. D.; MUSCARÁ, M. N., "Óxido Nitrico: propriedades e potenciais usos terapëuticos", *Quimica Nova*, v. 28, n. 6, p. 1046-1054, 2005).

In addition, nitric oxide acts as a transmitter of the peripherical nervous system and of the urogenital and gastrintestinal tracts.

The induced isoform of nitric oxide (iNOS) is calcium independent and is produced, in high concentrations, by means of activation with bacterial toxins, interpheron and interleukins.

In the defense system, NO is produced by mast cells, macrophages, Kupffer cells and neutrophyls, causing oxidative lesions in the target cell by means of attacking the proteins that are complexed to the membrane.

It is also known the technique to reduce the intestinal mucous membrane damage caused by the anti inflammatory active principles and, at the same time, guaranties a satisfactory absorption of such active principles, through the addition of arginine and similar aminoacids to the pharmaceutical compositions that present protective activity against intestinal mucous membrane damage (see Y. Kinouchi, N. Yata, Biol. Pharm. Bull., 19(3), pp. 375-378 (1996)).

In fact, it is known that L-arginine (NO precursor) protects the gastric mucous membrane from lesion formation, which mechanism probably involves an increase of the blood flux due to the dilatation of adjacent capillars (see KALIA, N. et al. "L-Arginine protects and exacerbates ethanol-induced rat gastric mucosal injury", Journal Gastroenterology and Hepatology, v. 15, n. 8, p. 915-24, 2000).

Studies performed with the introduction of L-arginine in the treatment with ibuprophen demonstrate a reduction of the oxidative stress and the infiltration of neutrophyls in the gastric mucous membrane, reducing the lesion caused by the anti inflammatory drug. This injury mechanism that depends of the microcirculation is of extreme importance for events of gastrintestinal toxicity caused by NSAI drugs that, in parallel to its therapeutic action, cause damage to the mucous membrane through inflammation mechanism and oxidative lesion monitored by the activity of mieloperoxidases, by the neutrophyllic activation rate, or by lipid peroxidation and activation of xantine oxidase, glutathione peroxidase and superoxide dismutase.

An explanation of the protective activity of L-arginine is the occurrence of a local action that is probably related to the inhibition of the oxidative stress derived from the xantine oxidases, but not to the blockage of the production of free radicals by nuclear polymorph leucocytes (see JIMENEZ, M. D. et al. "Role of L-arginine in ibuprofen-induced oxidative stress and neutrophil infiltration in gastric mucosa", Free Radical Research, v. 38, n. 9, p. 903-11, 2004).

It is also known that taurine acts in the inflammatory process due to its important activity which is of inhibiting the NO and E2-type prostaglandins production, acting in the suppression of the inducible nitric oxide synthase (iNOS) and in the expression of COX-2 (see LIU, Y. et al. "Taurine Chloramine Inhibits Production of Nitric Oxide and Prostaglandin E2 in Actiated C6 Glioma Cells by Supressing Inducible Nitric Oxide Synthase and Cyclooxigenase-2 expression", *Molecular Brain Research*, v. 59, p. 189-195, 1998), as well as in the inhibition of the peroxide ions (see CHAEKYUN, K. et al., "The Production of Superoxide Anion and Oxide by Cultured Murine Leukocytes and the Accumulation of TNF-α in the Conditioned Media is Inhibited by Taurine Chloramine", *Immunopharmacology*, v. 34, p. 89-95, 1996).

Another action of taurine is related to the reduction of the hyperanalgesic effects (see THOMAS, G. "Óxido Nitrico" In: Quimica Medicinal: Uma Introdução. Rio de Janeiro: Guanabara Koogan, p. 337-61, 2003), leading to normal levels of NO production, impeding, this way, the active and exacerbated presence of iNOS and inhibiting the arachidonic acid cascade. In fact, in 2001, Palumbo, Cioffi and D'Ischia requested patent for the NOS inhibitory compounds envisioning diverse uses, including inflammatory processes, reinforcing the safety expectation of this therapy (CAN 137:346227; AN 2002:894293; Italian application ITRM20000039 A, published in Jul. 24, 2001), confirming the results of Moncada and Higgs (see MONCADA, S.; HIGGS, E. A. "Molecular mechanisms and therapeutic strategies related to nitric oxide", FASEB Journal, v. 9, p. 1319-1330, 1995), about the utilization of nitric oxide synthase inhibitors, which represents an advance in the therapy of inflammatory conditions.

The inhibition of the oxidative stress can be explained by the systemic action of aminoacids. In this context, taurine have been presenting advantages related to the systemic action of gastro protection, probably through the suppression of free radicals derived from oxygen, which perform important physiopathologic role in the acute ulceration induced by NSAI drugs and ischemic reperfusion.

The experiment results using taurine as anti oxidant in the intragastric administration in rats pre-treated with 250 mg/kg or 500 mg/kg from 1 (one) to 3 (three) days before hemorrhagic lesion induction by 25 mg/kg of indometacin presented a lesion reduction with the inhibition of lipid peroxidation, besides the inhibition of neutrophyls activity (see SON, M. et al. "Protective effect of taurine on indometacin-induced gastric mucosal injury", Adv Exp Med Biol, v. 403, p. 147-55, 1996).

It is known, still, that taurine provides a significant reduction of the acid secretion and the increase of the bicarbonate liberation from the lumen due to mechanisms of regulation between the production of nitric oxide and prostaglandins, with a compensatory feedback being kept in the stomach (see TAKEUCHI, K. et al. "Nitric oxide and prostaglandins in regulation of acid secretory response in rat stomach following injury", Journal of Pharmacology Experimental and Therapeutic, v. 272, n. 1, p. 357-63, 1995).

In addition, it is known that the anti ulcerative activity is closely related to the improvement of the blood flux reduction in the mucous membrane due to the nitric oxide synthesis disturbance, in which the influence of anti ulcerogenic drugs is largely studied, as in the case of the [2,4-diamino-6-(2,5-dichlorophenyl)-S-thiazin]maleate. According to Takashi et al. (TAKASHI, K. et al. "Irsogladine prevents monochloramine-induced gastric mucosal lesions by improving the decrease in mucosal blood flow due to the disturbance of nitric oxide synthesis in rats", Journal of Pharmacological Sciences, v. 93, p. 314-20, 2003) the action proposal can be demonstrated through the use of constitutive nitric oxide synthase (cNOS) inhibitors or non selective inhibitors such as $N^G$-nitro-L-arginine methyl ester (L-NAME) and inducible nitric oxide synthase (iNOS) selective inhibitors, for example, the aminoguanidin, where the [2,4-diamino-6-(2,5-dichlorophenyl)-S-thiazin]maleate blocks the inhibitory action of cNOS without affecting the action of iNOS which is responsible for cellular recruiting.

As mentioned previously, the nitric oxide perform an important role in the protection of gastric ulceration induced by non steroidal anti inflammatory drugs by means of mechanisms that go beyond acid secretion, leading to a novel route for the treatment of gastric ulceration caused by anti inflammatory drugs. In pre clinic tests using the indometacin as control group of ulceration, it was verified that an 80% increase in gastric acidity with a 22% reduction of nitric oxide (measured as nitrite) occurs. On the other hand, the use of L-NAME does not affect gastric acidity, but causes a 50% reduction in the normal concentrations of nitric oxide and, consequently, the lesion rate doubles (see KHATTAB, M. M.; GAD, M. Z.; ABDALLAH, D. "Protective role of nitric oxide in indometacin-induced gastric ulceration by a mechanism independent of gastric acid secretion", Pharmacological Research, v. 43, n. 5, p. 463-67, 2001).

The peripherical vascular tonus homeostasis is of great importance in order to maintain the integrity of functional adjacent tissues where the manipulation of the process of NO up-down regulation can lead to thrombosis and ischemic complications, in case of low NO production.

It is important to highlight that, in analyzing the parameters of NO measurements in separate, its subfamilies and production moments must be related to enzymatic activity. This can be an answer to the fact that the use of a simple precursor, such as L-arginine it is not capable of preventing lesion formation in the gastric mucous membrane.

Therefore, the enzymatic substrate (L-arginine) can even increase the presence of NO in exacerbated form in pro inflammatory cells, which, in some way, makes this measure inefficient for blocking free radicals induced in the gastrintestinal inflammatory process.

In this context, taurine plays the role of mediator of a micro circulatory feed-back, besides acting in the inhibition of the enzymatic isoform induced in the inflammatory process. This isoform is responsible for the oxidative stress, then confirming the activity of taurine as gastrintestinal anti oxidant and anti inflammatory drug.

In the investigation of the gastro protector compounds, it was observed that taurine increases cellular resistance in 21%, with maintenance of membrane, mitochondria and nuclear damages integrity (see NAGY, L. et al. "Investigation of gastroprotective compounds at subcellular level in isolated gastric mucosal cells", American Journal Physiology and Gastrointestinal Liver Physiology, v. 279, n. G1, 201-08, 2000) which reinforces, through elucidation of gastric mucous membrane at subcellular level, the use of taurine as gastro protector compound.

Another proposal of mechanism of action for cytoprotection is based on the adaptation of the endogenous response mediated by prostaglandins without involving the protection pathway effect mediated by nitric oxide. This hypothesis was presented for the activity of L-arginine (NO precursor) against gastric injury, caused in rats, induced by the oral administration of hydrochloric acid (see TAKEUCHI, K. et al. "Cytoprotective action of L-arginine against HCL-induced gastric injury in rats: Involvement of nitric oxide?", Japan Journal Pharmacology, v. 61, p. 13-21, 1993). The advantage of taurine over L-arginine becomes more evident from the analysis of the results of its use in the reduction of damages to the gastric mucous membrane, because it does not present NO precursor activity.

Although the participation of prostaglandins and nitric oxide in the inhibition of lesion formation induced by necrotic agents is known, there is no clear correlation with the importance degree of these mediators. Nitric oxide inhibition experiments (L-NAME) with supplement of $E_2$ 16,16-dimethyl prostaglandin do not cause damage. On the other hand, prostaglandin inhibition with supplement of nitric oxide donor is not sufficient for maintenance of gastric mucous membrane integrity (see UCHIDA, M. et al. "Nitric oxide donating compounds inhibit HCl-induced gastric mucosal lesions mainly via prostaglandin", Japan Journal Pharmacology, v. 85, p. 133-38, 2001). This study confirms the most evident adverse effect in the therapeutic use of anti inflammatory drugs, as well as the difficulty in lesion reversion or gastroprotection.

Taurine acts in the inflammatory process due to its important activity in inhibiting NO and E2-type prostaglandins ($PGE_2$) production and in acting in the suppression of inducible nitric oxide synthase (iNOS) and in the expression of type-2 cyclooxygenase (see LIU, Y. et al. "Taurine chloramine inhibits production of nitric oxide and prostaglandin $E_2$ in activated C6 glioma cells by suppressing inducible nitric oxide synthase and cyclooxigenase-2 expression", Molecular Brain Research, v. 59, p. 189-195, 1998), as well as in the inhibition of peroxide ions production (see CHAEKYUN, K. et al. "The production of superoxide anion and oxide by cultured murine leukocytes and the accumulation of TNF-$\alpha$ in the conditioned media is inhibited by taurine chloramine", Immunopharmacology, v. 34, p. 89-95, 1996).

Many attempts to interfere in the process of gastric lesion formation caused by the NSAI drugs have been made. In the U.S. Pat. No. 7,008,920 it is described the pharmaceutical association between NSAI drugs, bile acid salts and taurine or polyamines in order to reduce the gastrintestinal damage induces by drugs and the increase of their water-solubility.

It is also known that taurine, besides acting against gastric damage (see SENER, G. et al. "Protective effect of taurine against alendronate-induced gastric damage in rats", Fundamental & Clinical Pharmacology, v. 19, p. 93-100, 2004), it also attenuates kidney hypertension (see HAGAR, H. H.; ETTER, E. E.; ARAFA, M. "Taurine attenuates hypertension and renal dysfunction induced by cyclosporine A in rats", Clinical and Experimental Pharmacology and Physiology, v. 33, p. 189-196, 2006).

Another important aspect in the search for compounds that attenuate the adverse effects of NSAI drugs and potentate the beneficial effects of these drugs is the development of viable processes of obtaintion under technical and economical point of view. Therefore, numerous researches are being developed in order to obtain novel compounds using, mainly, the molecular modification techniques. Among the obtaintion processes, it is of great importance the latentiation that has the purpose of developing the prodrugs that consist in inactive vehicle forms and that release the drug in vivo after biotransformation (see WERMUTH, C. G. "The Practice of Medicinal Chemistry", London: Academic Press, $2^a$ ed, 2003. 768 pages; KROGSGAARD-LARSEN, P., BUNDGAARD, H. "A textbook of drug design and the development", Harwood: Academic Publish, 1991, 643 pages; SILVA, A. T. A. et al. "Advances in prodrug design", Medicinal Chemistry. v. 5, n. 10, p. 893-914, 2005).

The most current therapeutic chemical compounds have been produced through the latentiation of the original drug, particularly through estherification and amides formation. In a simpler way, it can be said that latentiation is an organic synthesis process that seeks to modify the molecule of an active compound or original drug in order to optimize its pharmacokinetic properties and/or reduce its toxicity.

In the past few years, latentiation has become one of the main tools for the development of chemiotherapic drugs used in the treatment of the major current diseases such as cancer and Acquired Immunodeficiency Syndrome—AIDS. The search for latent drugs is justified by at least one of the following reasons: (i) minimize the pharmacokinetic inconveniences belonging to the original drug, (ii) reduce the high toxicity of the original drug, (iii) perfect the weak chemical stability of the original drug, (iv) improve the water-solubility of the original drug, (v) reduce the inconveniences of odor and taste of the original drug and (vi) make it possible the obtaintion of difficult pharmaceutical formulations due to the original drug.

The latent drugs, called prodrugs, correspond to original drugs that are chemically transformed to an inactive derived compound through chemical reactions, enzymatic reactions or both. The prodrug is converted into the original drug inside the organism prior or after reaching its action spot.

The prodrug can be defined as any compound that undergoes biotransformation before exhibiting its pharmacologic effects. The prodrug as well as the analog of a drug present similar chemical structures, however the biological properties of these compounds differ from the original drug regarding: (i) the activity, (ii) the potency, (iii) the bioavailability, (iv) the synthesis process, (v) the action spectrum, and (vi) therapeutic index. The prodrug differs from the analog drug due to the in vivo hydrolysable chemical bond and the transporter group.

Among the various prodrugs obtaintion methods, estherification is the most employed one, followed by amide, imide and carbamate formation. Currently, drug functional groups can be modified through chemical reactions producing reversible groups heavily used in the development of prodrugs.

Countless substitutions in known molecules as well as novel NSAI-derived drugs are described in the state of the technique seeking to improve not only their adverse effects as well as their anti inflammatory potential. For example, the U.S. Pat. No. 5,905,073 patent described 5-ASA and other NSAI-derived prodrugs for treating ulcerative colitis.

Among the commercially available NSAI drugs, diclophenac is one of the most used anti inflammatory drugs. In fact, diclophenac, discovered in 1966 and described in the U.S. Pat. No. 3,558,690, is one of the best seller drugs in the world and its efficacy and safety is established in the anti inflammatory therapy field. Various substitutions have also been made in 2-arylaminophenylacetic acids in order to reduce the deleterious side effects of this active principle, being described in several patent documents, such as, for example U.S. Pat. Nos. 3,652,762; 4,173,577; 4,166,128; 4,704,468; 5,475,139; WO 9404484; WO 9709977; WO 9600716 and DE 345011.

The aceclophenac is an example of diclophenac prodrug, described in the U.S. Pat. No. 4,548,952, obtained through the estherification of the carboxylic group by an small alkyl chain, in an attempt of reducing the deleterious effects in the gastrintestinal tract when used in anti inflammatory therapies. For example, the U.S. Pat. No. 6,451,858 described estherifications in 2-arylaminophenylacetic acids as an attempt of increasing its selectivity towards COX-2.

Other modifications in the diclophenac molecule were performed in order to reduce undesired side effects or to increase its bioavailability to make other administration options besides oral viable, being cited: (i) the U.S. Pat. No. 4,704,468 that describes double diclophenac prodrugs linked by polyethylene glycol-derived compounds in order to reduce the gastric effects and (ii) the U.S. Pat. No. 5,792,786 that describes NSAI drugs estherifications with long chained fatty acids in order to increase their bioavailability in topic use pharmaceutical forms.

Still in order to reduce the prejudicial effects caused by NSAI drugs in patients presenting inflammatory disturbances, more recently, researches has been directed to the a more detailed study of the functions performed by nitric oxide in the biological systems. In this context, the U.S. Pat. No. 5,597,847 describes 2-arylaminophenylacetic acids-derived compounds that were nitrated in order to increase their anti inflammatory potential seeking to provide nitric oxide in the inflammatory process. In a similar way, prodrugs with NO local release are described in the patent document WO 2006125016.

The WO 9109831 document describes NSAI-derived prodrugs with acid groups obtained through anhydride formation among groups present in the NSAI drug itself or in different NSAI drugs, such as ASA, SA (salicylic acid), sulindac, cetoprophen, indometacin, naproxen, fenoprophen, ibuprophen, diflunisal, tolmetin, flurbiprophen, suprophen.

Other prodrug obtaintion examples are presented in the U.S. Pat. No. 5,681,964 that describes indometacin estherifications, resulting in reduction of gastric damages; in the U.S. Pat. Nos. 5,607,966 and 5,811,438 that describe ester derived compounds and indometacin amides used as antioxidants and 5-lipoxygenase inhibitors, without, however, presenting COX-2 selectivity; in the U.S. Pat. No. 6,399,647 that describes indometacin-derived sulphonamidic compounds presenting an increase in COX-2 selectivity; and in the U.S. Pat. No. 6,887,903 that describes sulphonamidic derived compounds that act in other pathways of the inflammatory process as signaling molecules of nuclear polymorph neutrophyls and other interleukins.

In spite of this diversity of NSAI prodrugs have presented advantages regarding the original drugs, there are still various deleterious effects that limit their use.

Taurine and other specific aminoacids present themselves as interesting drug transporters, enabling an improvement not only in physico-chemical, but also reducing its adverse effects. The U.S. Pat. No. 5,059,699 presents taxol-derived compounds (antineoplasic) and taurine to increase its water-solubility, leading to the increase of its bioavailability and stability in chemiotherapeutical formulas. Other formula improvement examples using taurine are based on salicylate-derived compounds (SA and ASA) or in sulphonamidic-derived compounds as described in the documents JP68003293 and JP68004331.

The limitations and disadvantages of known prodrugs and drugs led to the search for novel active principles disclosed herein, which minimizes the deleterious effects of the NSAI drugs. Hence, the present invention results from the knowledge of mechanisms of action of the anti inflammatory drugs described by the therapeutic field, exploring their potential in the use of NSAI-derived drugs during chronic anti inflammatory treatments.

Therefore, the objective of the present invention is to is the pharmacotherapeutic that involves acute and chronic treatments with anti inflammatory drugs seeking reduce or annul the adverse effects of gastric ulceration from the discovery that aminoacids associated to anti inflammatory administered orally reduce the extension of the gastric lesion, where taurine present an important role in this mechanism, particularly regarding to its participation in the pro inflammatory cytokines regulation process.

SUMMARY OF THE INVENTION

The present invention has as its objective to reduce the side and adverse effects of the non-steroidal anti inflammatory (NSAI) drugs by providing novel compounds based in taurine-derived ones. More specifically, the invention has as its foundation the introduction of an amidic bond between the molecules of NSAIs and taurine, resulting in novel compounds of the invention which adjuvant activity results by nitric oxide production inhibition induced in the inflammatory process by specific enzymes present in the macrophages and neutrophyls (inducible nitric oxide synthase—iNOS) as well as by cyclooxygenase inhibition and probably by the active principles slow in vivo release leading to a toxicity control of NSAI drugs with the maintenance of their anti inflammatory activity.

A first embodiment of the present invention is regarding the taurine-derived compounds, which taurine is directly linked by means of an amide bond or through an spacing group to a selected compound from a group of non-steroidal anti inflammatory compound, called taurine-derived and presenting Formula (I):

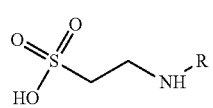

(I)

which R means the component with non-steroidal anti inflammatory activity.

In a second embodiment, the present invention provides an obtaintion process of novel Formula (I) compounds, its salts, solvates, hydrates, enantiomers, diasteroisomers and polymorphs, comprising the taurine reaction with a compound belonging to the group of non-steroidal anti inflammatory (NSAI) drugs, in the presence of an appropriate catalyzer, in order to obtain a taurine-derived compound through direct bond or by the means of an spacing group of taurine to NSAI.

In a third embodiment, the present invention is regarding the pharmaceutical compositions comprising: (a) a taurine-derived compound with anti inflammatory activity from the non-steroidal type, (b) optionally, an appropriate active principle for treating a medical condition involving an inflammatory disturbance and (c) a pharmaceutical-acceptable vehicle.

DETAILED DESCRIPTION OF THE INVENTION

Figure 1:
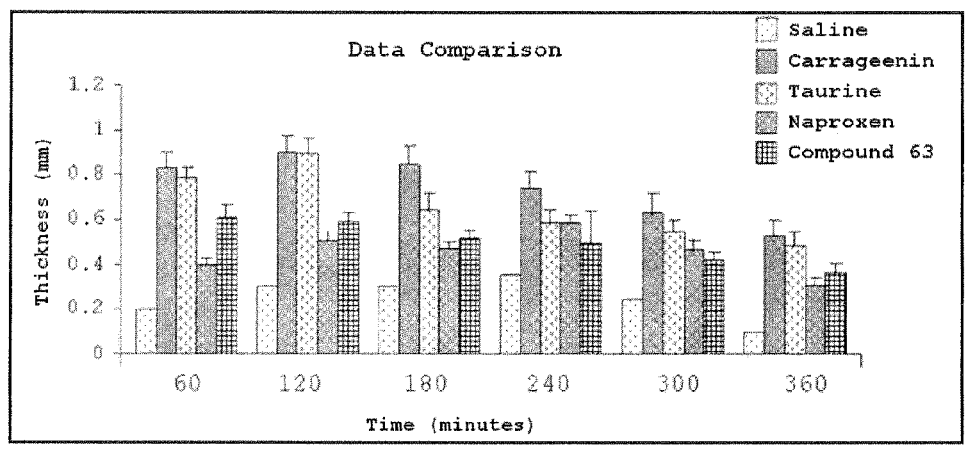
FIG. 1 shows a comparative assay of the anti inflammatory activity per rat's paw using taurine, naproxen and its derived compound (Compound 63, embodiment of the invention corresponding to Example 2).

The compounds of the invention are derived from taurine, obtained from de formation of amidic bonds with non-steroidal anti inflammatory (NSAI) drugs, directly as well as through a provided spacing agent.

Following, some definitions are provided, in order to facilitate the comprehension of the present invention.

Taurine—2-aminoethanesulfonic acid

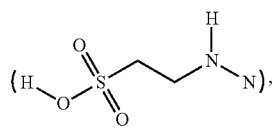

non-essential aminoacid which is one of the most abundant aminoacids in the human body.

Amidic bond—chemical bond of the —NHCOY-type between the component with non-steroidal anti inflammatory activity (NSAI) (drug) and taurine (transporter).

Non-steroidal anti inflammatory (NSAI) drugs—they are substances with anti inflammatory, analgesic and antipyretic effect. The NSAI drugs act in the organism blocking the prostaglandins synthesis and include compounds as: salycilates, pyrazolons and analogs, derived indoleacetics, derived arilacetics, derived arylpropionics, oxycams and phenamates.

Spacing agent—intermediate chemical group that establishes the bond between the drug and the transporter. In the chemical release of the drug, the use of an spacing agent allows better and higher access of the enzyme; this way, the release of the active portion is facilitated which consists in the major factor in the manifestation of the biological activity.

Taurine-derived compounds—includes the isomers, enantiomers, analogs and prodrugs resultant from the bond of taurine with a selected compound from the group of NSAI drugs through a direct amidic bond or by means of an spacing agent.

The compounds of the present invention are compounds represented by the general Formula (I):

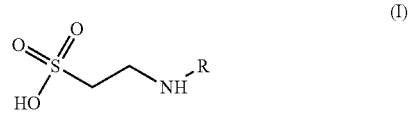

where the taurine component:

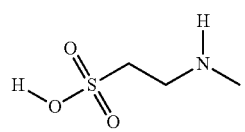

is linked, directly or through an spacing agent, to NSAI drug, forming and amidic bond of the —NHCOY-type, which the —COY group correspond to the R substituent of the general Formula (I).

The NSAI components of the invention can be any component belonging to the non-steroidal anti inflammatory group. Preferentially, the NSAI component out of the compounds of the invention can be any R substituent as defined in Table 1.

TABLE 1

Preferred Formula (I) Compounds

| R Substituent | Formula (I) Compound |
|---|---|
| Derived from 2-[2-(2,6-dichlorophenylamino) phenyl] acetic acid | Compound 1: 2-{2-[2-(2,6-dichlorophenylamino) phenyl] acetamide} ethanesulfonic acid |
| derived from 2-[(2,6-dichloro-3-methylphenyl)amino] benzoic acid | Compound 2: 2-{[(2,6-dichloro-3-methylphenyl)aminobenzoil] amide} ethanesulfonic acid |

TABLE 1-continued

Preferred Formula (I) Compounds

| R Substituent | Formula (I) Compound |
|---|---|
| 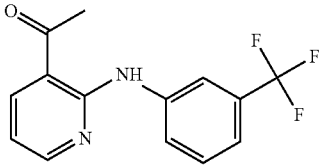<br>derived from 2-{[3-(trifluoromethyl)phenyl]amino} nicotinic acid | 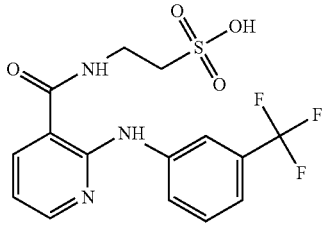<br>Compound 3: 2-{[3-(trifluoromethyl)phenyl]amino}nicotinoyl] amide} ethanesulfonic acid |
| 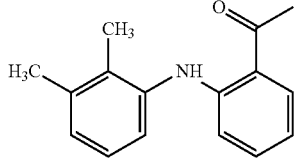<br>derived from 2-[(2,3-dimethylphenyl) amino] benzoic acid | 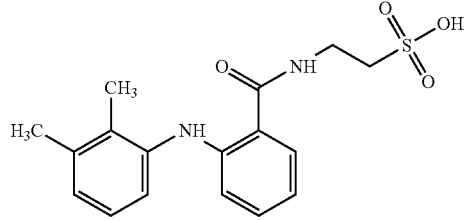<br>Compound 4: 2-{[(2,3-dimethylphenyl) amino]benzoyl] amide} ethanesulfonic acid |
| 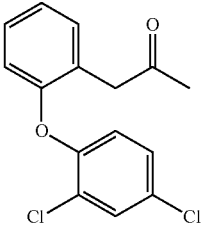<br>derived from 2-[(2,4-dichlorophenoxy) phenyl] acetic acid | 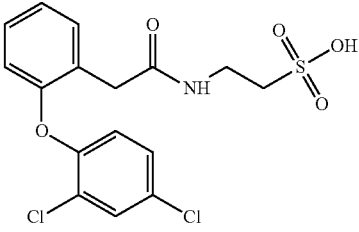<br>Compound 5: 2-{[(2,4-dichlorophenoxy) phenyl] acetyl] amide} ethanesulfonic acid |
| 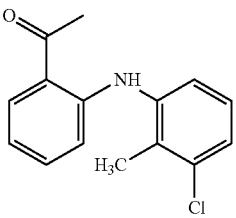<br>derived from 2-[(3-chloro-2-methylphenyl)amino] benzoic acid | 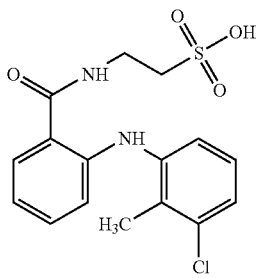<br>Compound 6: 2-{[(3-chloro-2-methylphenyl)amino] benzoyl] amide} ethanesulfonic acid |

TABLE 1-continued

Preferred Formula (I) Compounds

| R Substituent | Formula (I) Compound |
|---|---|
| 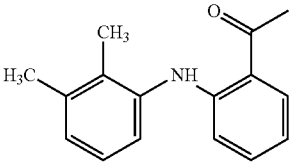 derived from 2-[(2,3-dimethylphenyl) amino] benzoic acid | 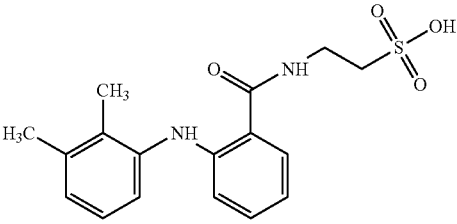 Compound 7: 2-{[(2,3-dimethylphenyl) amino]benzoyl] amide} ethanesulfonic acid |
| 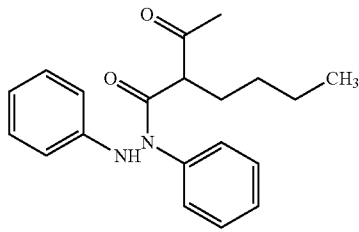 derived from 2-[1,2-diphenyl-hydrazino) carbonyl] hexanoic acid | 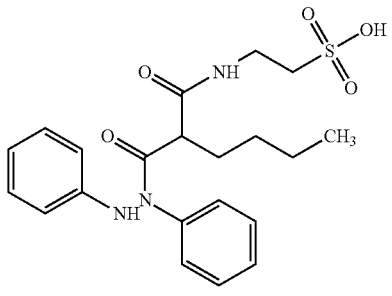 Compound 8: 2-{[(1, 2-diphenyl-hydrazino) carbonyl] hexanoyl] amide} ethanesulfonic acid |
| 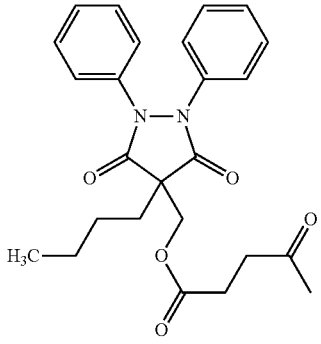 derived from 4-[(4-butyl-3,5-dioxo-1,2-diphenylpyrazolidin-4-yl) methoxy]-4-oxobutanoic acid | 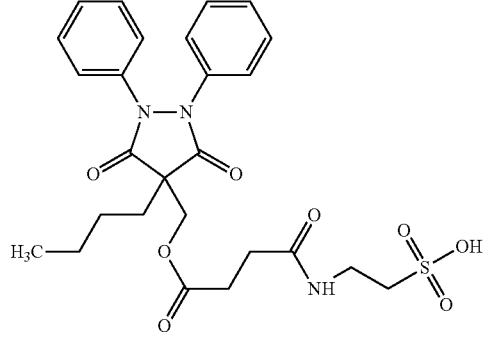 Compound 9: 4-{[(4-butyl-3,5-dioxo-1,2-diphenylpyrazolidin-4-yl) methoxy]-4-oxobutanoyl] amide} ethanesulfonic acid |
| 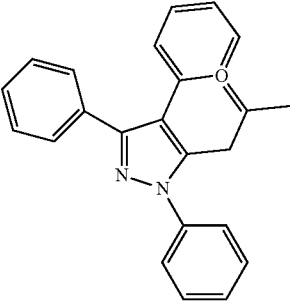 derived from (1,3,4-triphenyl-1H-pyrazol-5-yl)acetic acid | 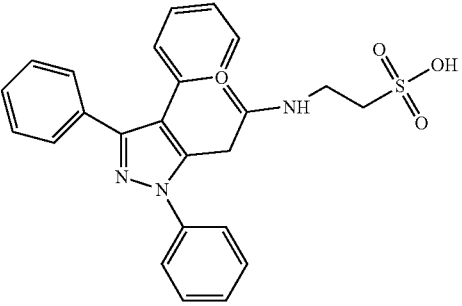 Compound 10: {[(1,3,4-triphenyl-1H-pyrazol-5-yl)acetyl] amide} ethanesulfonic acid |

TABLE 1-continued

Preferred Formula (I) Compounds

| R Substituent | Formula (I) Compound |
|---|---|
| 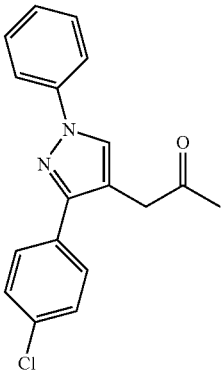 derived from [3-(4-chlorophenyl)-1-phenyl-1H-pyrazol-4-yl] acetic acid | 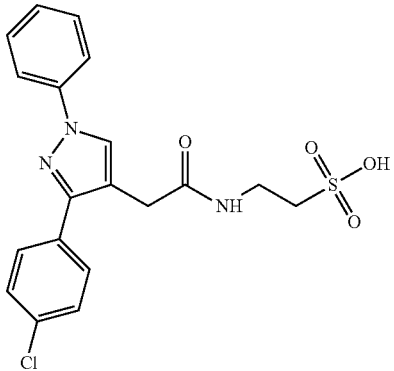 Compound 11: {[[3-(4-chlorophenyl)-1-phenyl-1H-pyrazol-4-yl] acetyl amide} ethanesulfonic acid |
| 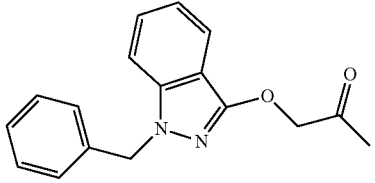 derived from [(1-benzyl-1H-indazol-3-yl)oxy] acetic acid | 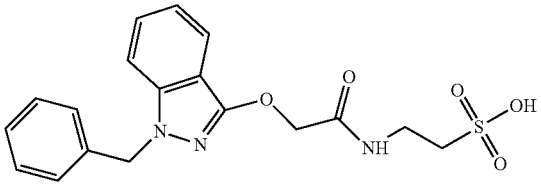 Compound 12: {[(1-benzyl-1H indazol-3-yl)oxy] acetyl] amide} ethanesulfonic acid |
| 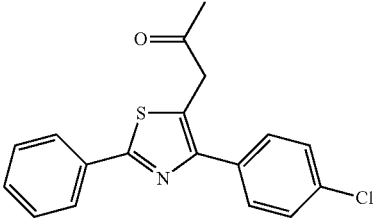 derived from [4-(4-chlorophenyl)-2-phenyl-1,3-thiazol-5-yl] acetic acid | 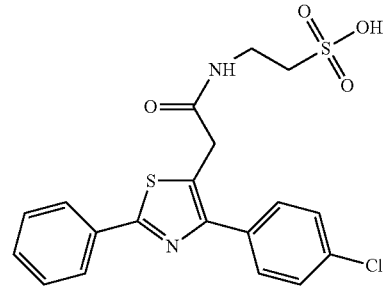 Compound 13: {[[4-(4-chlorophenyl)-2-phenyl-1,3-thiazol-5-yl] acetyl] amide} ethanesulfonic acid |
| 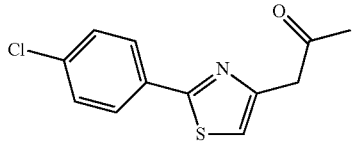 derived from [2-(4-chlorophenyl)-1,3-thiazol-4-yl] acetic acid | 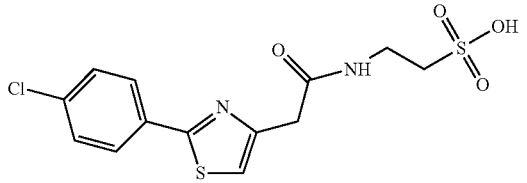 Compound 14: {[[2-(4-chlorophenyl)-1,3-thiazol-4-yl] acetyl] amide} ethanesulfonic acid |

TABLE 1-continued

Preferred Formula (I) Compounds

| R Substituent | Formula (I) Compound |
|---|---|
| derived from 3-(4,5-diphenyl-1,3-oxazol-2-yl)propanoic acid | Compound 15: 3-{[(4,5-diphenyl-1,3-oxazol-2-yl)propanoyl] amide} ethanesulfonic acid |
| derived from [1-(4-chlorophenyl)-2,5-dimethyl-1H-pyrol-3-yl] acetic acid | Compound 16: {[[1-(4-chlorophenyl)-2,5-dimethyl-1H-pyrol-3-yl] acetyl] amide} ethanesulfonic acid |
| derived from 2-amino-6-benzyl-4,5,6,7-tetrahydrothieno[2,3-c] pyridine-3-carboxylic acid | Compound 17: 2-{[amino-6-benzyl-4,5,6,7-tetrahydrothieno[2,3-c] pyridine-3-carboxylyl] amide} ethanesulfonic acid |
| derived from [2-(aminocarbonyl) phenoxy] acetic acid | Compound 18: {[[2-(aminocarbonyl) phenoxy] acetyl] amide} ethanesulfonic acid |
| derived from 2,5-dihydroxybenzoic acid | Compound 19: [(2,5-dihydroxybenzoyl) amide] ethanesulfonic acid |

TABLE 1-continued

Preferred Formula (I) Compounds

| R Substituent | Formula (I) Compound |
|---|---|
| derived from 2-(sulphooxy) benzoic acid | Compound 20: {[2-(sulphooxy) benzoyl] amide} ethanesulfonic acid |
| derived from 2-[(2-hydroxybenzoyl)oxy] benzoic acid | Compound 21: 2-{[(2-hydroxybenzoyl)oxy] benzoyl] amide} ethanesulfonic acid |
| derived from 2-[(2-phenylethyl)amino] benzoic acid | Compound 22: 2-{[(2-phenylethyl)amino] benzoyl] amide} ethanesulfonic acid |
| derived from 5-[(2-phenyl-4,5-dihydro-3H-benzo[e]-1H-indole-2-(2-hydroxybenzoic acid) | Compound 23: 5-{[(2-phenyl-4,5-dihydro-3H-benzo[e]-1H-indole-2-(2-hydroxybenzoyl) amide]} ethanesulfonic acid |

TABLE 1-continued

Preferred Formula (I) Compounds

| R Substituent | Formula (I) Compound |
|---|---|
| 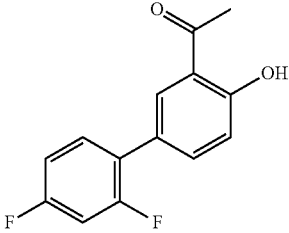<br>derived from 2',4'-difluoro-4-hydroxy-1,1'-diphenyl-3-carboxylic acid | 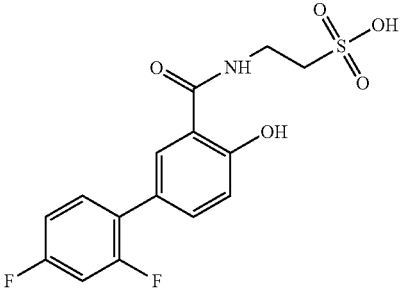<br>Compound 24: acid [(2',4'-difluoro-4-hydroxy-1,1'-diphenyl-3-carboxylyl) amide] ethanesulfonic |
| 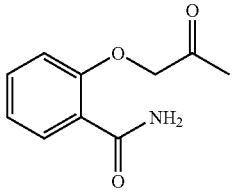<br>derived from [2-(aminocarbonyl) phenoxy] acetic acid | 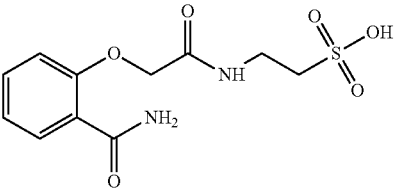<br>Compound 25: {[[2-(aminocarbonyl) phenoxy] acetyl] amide} ethanesulfonic acid |
| 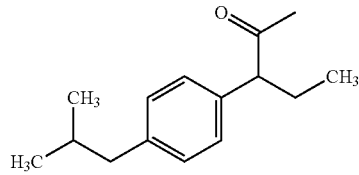<br>derived from 2-(4-isobuthylphenyl) butanoic acid | 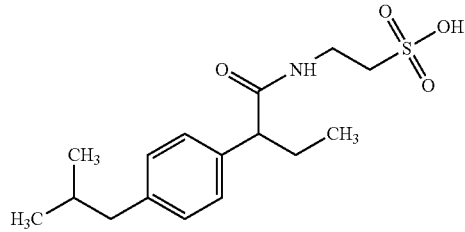<br>Compound 26: 2-{[2-(4-isobuthylphenyl) butanoyl] amide} ethanesulfonic acid |
| 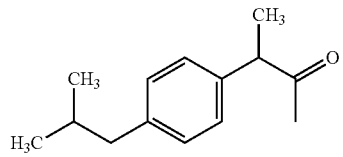<br>derived from 2-(4-isobuthylphenyl) propanoic acid | 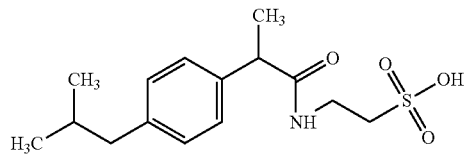<br>Compound 27: [2-(4-isobuthylphenyl) propanoyl] amide ethanesulfonic acid |

TABLE 1-continued

Preferred Formula (I) Compounds

| R Substituent | Formula (I) Compound |
|---|---|
| derived from 2-[4-(thien-2-yl-carbonyl) phenyl] propanoic acid | Compound 28: {2-[4-(thien-2-yl-carbonyl) phenyl] propanoyl} amide ethanesulfonic acid |
| derived from 2-(3-phenoxyphenyl) propanoic acid | Compound 29: {2-(3-phenoxyphenyl) propanoyl} amide ethanesulfonic acid |
| derived from chloro (3-chloro-4-cyclo-hexylphenyl) acetic acid | Compound 30: [chloro (3-chloro-4-cyclo-hexyphenyl) acetyl] amide ethanesulfonic acid |
| derived from 4-(3-chloro-4-cyclo-hexyl phenyl)-4-oxobutanoic acid | Compound 31: [4-(3-chloro-4-cyclo-hexyl phenyl)-4-oxobutanoyl] amide ethanesulfonic acid |
| derived from 6-chloro-5-cyclo-hexylindane-1-carboxilic acid | Compound 32: (6-chloro-5-cyclo-hexylindane-1-carboxyl) amide ethanesulfonic acid |

TABLE 1-continued

Preferred Formula (I) Compounds

| R Substituent | Formula (I) Compound |
|---|---|
| 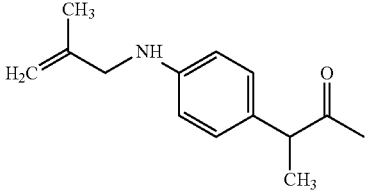 derived from 2-{4-[(2-methylprop-2-enil) amino] phenyl}propanoic acid | 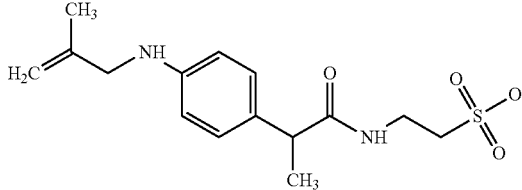 Compound 33: 2-{4-[(2-methylprop-2-enil) amino] phenyl-propanoyl} amide ethanesulfonic acid |
| 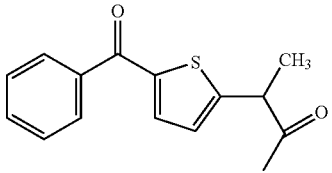 derived from 2-(5-benzoylthien-2-yl) propanoic acid | 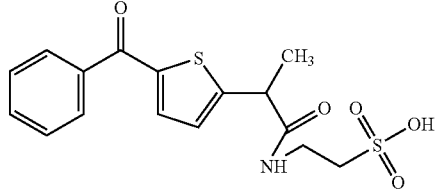 Compound 34: [2-(5-benzoylthien-2-yl) propanoyl] amide ethanesulfonic acid |
| 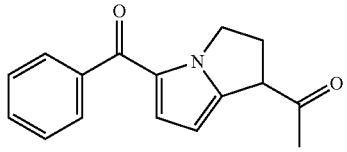 derived from 5-benzoyl-2,3-dihydro-1H-pyrolizine-1-carboxylic acid | 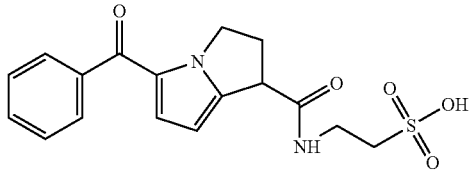 Compound 35: (5-benzoyl-2,3-dihydro-1H-pyrolizine-1-carboxyl) amide ethanesulfonic acid |
| 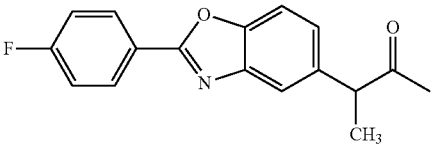 derived from 2-[2-(4-fluorophenyl)-1,3-benzoxazol-5-yl] propanoic acid | 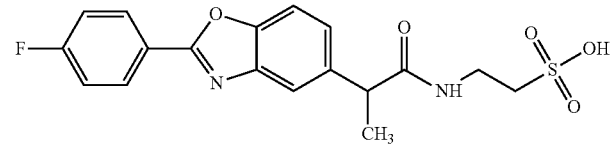 Compound 36: {2-[2-(4-fluorophenyl)-1,3-benzoxazol-5-yl] propanoyl} amide ethanesulfonic acid |
| 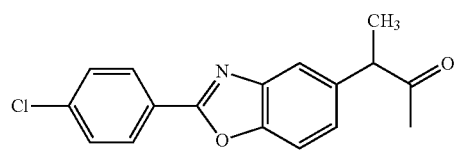 derived from 2-[2-(4-chlorophenyl)-1,3-benzoxazol-5-yl] propanoic acid | 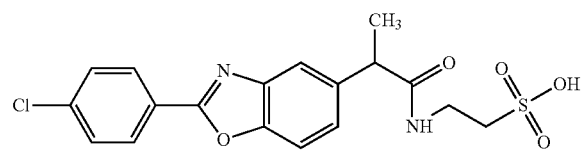 Compound 37: {2-[2-(4-chlorophenyl)-1,3-benzoxazol-5-yl] propanoyl} amide ethanesulfonic acid |
| 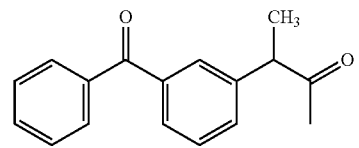 derived from 2-(3-benzoylphenyl) propanoic acid | 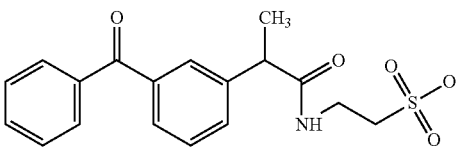 Compound 38: [2-(3-benzoylphenyl) propanoyl] amide ethanesulfonic acid |

TABLE 1-continued

Preferred Formula (I) Compounds

| R Substituent | Formula (I) Compound |
|---|---|
| 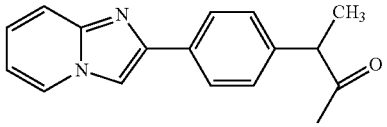 derived from 2-(4-imidazo[1,2-a]pyridin-2-yl phenyl) propanoic acid | 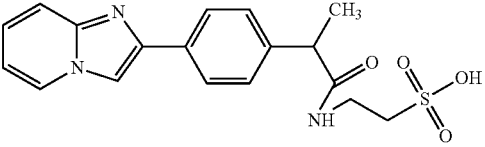 Compound 39: [2-(4-imidazo[1,2-a]pyridin-2-yl phenyl) propanoyl] amide ethanesulfonic acid |
| 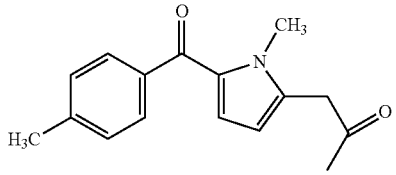 derived from [1-methyl-5-(4-methylbenzoyl)-1H-pyrol-2yl] acetic acid | 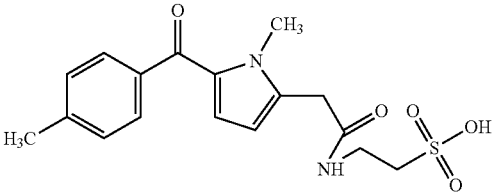 Compound 40: {[1-methyl-5-(4-methylbenzoyl)-1H-pyrol-2-yl] acetyl} amide ethanesulfonic acid |
| 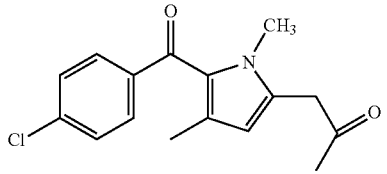 derived from [5-(4-chlorobenzoyl)-1,4-dimethyl-1H-pyrol-2-yl] acetic acid | 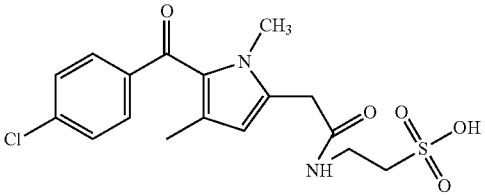 Compound 41: {[5-(4-chlorobenzoyl)-1,4-dimethyl-1H-pyrol-2-yl] acetyl} amide ethanesulfonic acid |
| 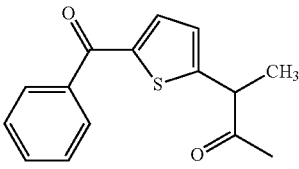 derived from 2-(5-benzoylthien-2-yl) propanoic acid | 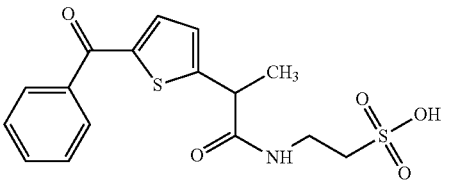 Compound 42: [2-(5-benzoylthien-2-yl) propanoyl] amide ethanesulfonic acid |
| 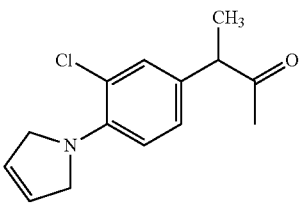 derived from 2-[3-chloro-4-(2,5-dihydro-1H-pyrol-1-yl)phenyl] propanoic acid | 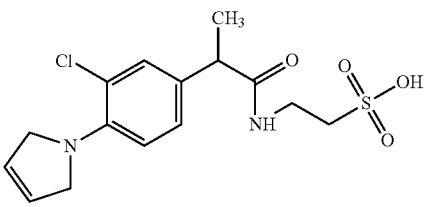 Compound 43: {2-[3-chloro-4-(2,5-dihydro-1H-pyrol-1-yl)phenyl] propanoyl} amide ethanesulfonic acid |

TABLE 1-continued

Preferred Formula (I) Compounds

| R Substituent | Formula (I) Compound |
|---|---|
| 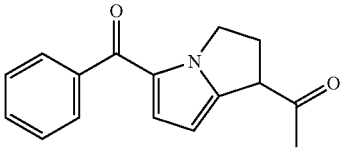 derived from 5-benzoyl-2,3-dihydro-1H-pyrolizine-1-carboxylic acid | 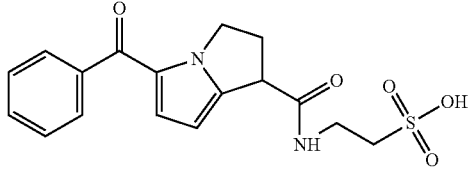 Compound 44: (5-benzoyl-2,3-dihydro-1H-pyrolizine-1-carboxyl) amide ethanesulfonic acid |
| 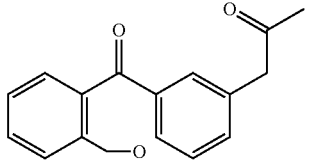 derived from (11-oxo-6,11-dihydrodi benzo[b,e]oxepin-2-yl) acetic acid | 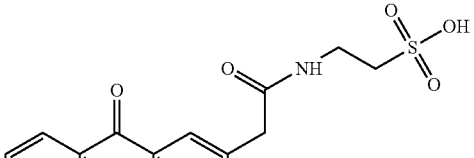 Compound 45: [(11-oxo-6,11-dihydrodi benzo[b,e]oxepin-2-yl)acetyl] amide ethanesulfonic acid |
| 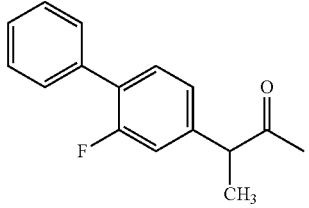 derived from 2-(2-fluoro-1,1'-diphenyl-4-yl) propanoic acid | 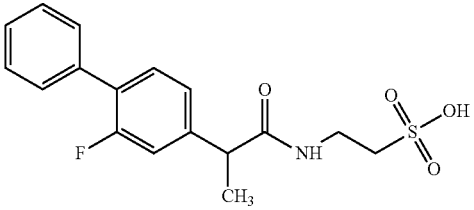 Compound 46: [2-(2-fluoro-1,1'-diphenyl-4-yl) propanoyl] amide ethanesulfonic acid |
| 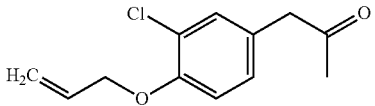 derived from [4-(allyloxy)-3-chlorophenyl] acetic acid | 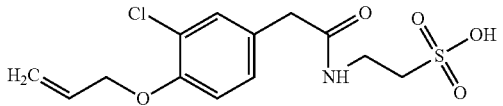 Compound 47: {[4-(allyloxy)-3-chlorophenyl] acetyl} amide ethanesulfonic acid |
| 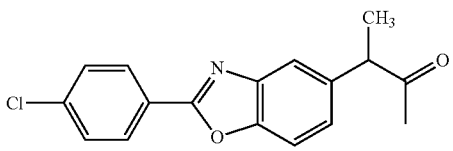 derived from 2-[2-(4-chlorophenyl)-1,3-benzoxazol-5-yl] propanoic acid | 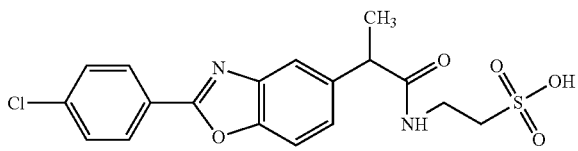 Compound 48: {2-[2-(4-chlorophenyl)-1,3-benzoxazol-5-yl] propanoyl} amide ethanesulfonic acid |

TABLE 1-continued

Preferred Formula (I) Compounds

| R Substituent | Formula (I) Compound |
|---|---|
| derived from 2-[4-(1-oxo-1,3-dihydro-2H-isoindole-2-yl)phenyl] propanoic acid | Compound 49: {2-[4-(1-oxo-1,3-dihydro-2H-isoindole-2-yl)phenyl] propanoyl} amide ethanesulfonic acid |
| derived from 6-chloro-5-cyclo-hexylindane-1-carboxylic acid | Compound 50: (6-chloro-5-cyclo-hexylindane-1-carboxyl) amide ethanesulfonic acid |
| derived from 2-[4-(2,5-dihydrothien-2-yl carbonyl)phenyl] propanoic acid | Compound 51: {2-[4-(2,5-dihydrothien-2-yl carbonyl)phenyl] propanoyl} amide ethanesulfonic acid |
| derived from 2-(5-benzoylthien-2-yl) propanoic acid | Compound 52: [2-(5-benzoylthien-2-yl) propanoyl] amide ethanesulfonic acid |

TABLE 1-continued

Preferred Formula (I) Compounds

| R Substituent | Formula (I) Compound |
|---|---|
| 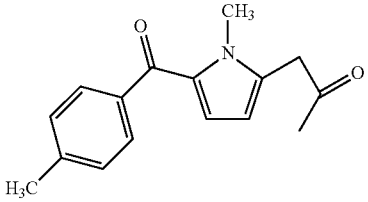 derived from [1-methyl-5-(4-methylbenzoyl)-1H-pyrol-2-yl] acetic acid | 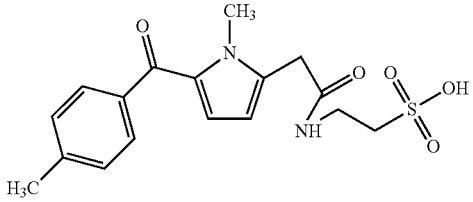 Compound 53: {[[1-methyl-5-(4-methylbenzoyl)-1H-pyrol-2-yl] acetyl] amide} ethanesulfonic acid |
| 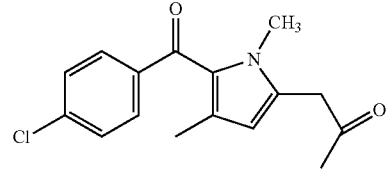 derived from [1-(4-chlorophenyl)-2,5-dimethyl-1H-pyrol-3-yl] acetic acid | 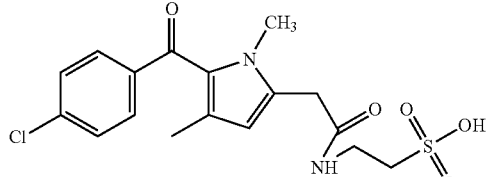 Compound 54: {[[1-(4-chlorophenyl)-2,5-dimethyl-1H-pyrol-3-yl] acetyl] amide} ethanesulfonic acid |
| 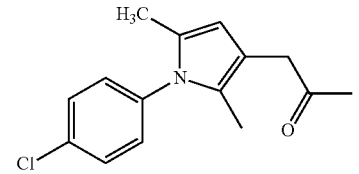 derived from [1-(4-chlorophenyl)-2,5-dimethyl-1H-pyrol-3-yl] acetic acid | 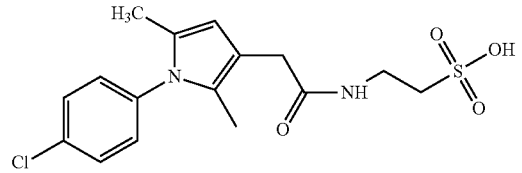 Compound 55: {[[1-(4-chlorophenyl)-2,5-dimethyl-1H-pyrol-3-yl] acetyl] amide} ethanesulfonic acid |
| 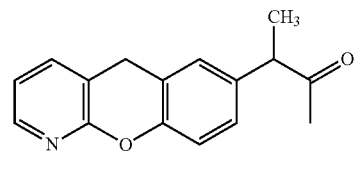 derived from 2-(5H-chromene[2,3-b]pyridin-7-yl) propanoic acid | 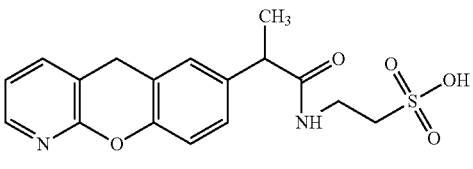 Compound 56: 2-{[(5H-chromene[2,3-b]pyridin-7-yl) propanoyl] amide} ethanesulfonic acid |
| 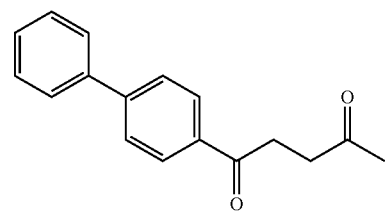 derived from 4-(1,1'-biphenyl-4-yl)-4-oxobutanoic acid | 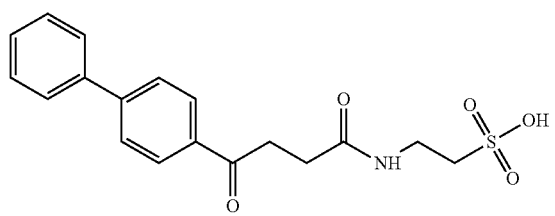 Compound 57: 4-{[1,1'-biphenyl-4-yl)-4-oxobutanoyl] amide} ethanesulfonic acid |

TABLE 1-continued

Preferred Formula (I) Compounds

| R Substituent | Formula (I) Compound |
|---|---|
| derived from 1,1'-biphenyl-4-yl acetic acid | Compound 58: [(1,1'-biphenyl-4-yl acetyl) amide] ethanesulfonic acid |
| derived from 3-(4,5-diphenyl-1,3-oxazol-2-yl)propanoic acid | Compound 59: 3-{[(4,5-diphenyl-1,3-oxazol-2-yl)propanoyl] amide} ethanesulfonic acid |
| derived from 2-[4-(1-oxo-1,3-dihydro-2H-isoindole-2-yl) phenyl] propanoic acid | Compound 60: 2-{[[4-(1-oxo-1,3-dihydro-2H-isoindole-2-yl) phenyl] propanoyl] amide} ethanesulfonic acid |
| derived from 4-[(4-chlorophenyl)-2-phenyl-1,3-thiazol-5-yl] acetic acid | Compound 61: 4-{[[(4-chlorophenyl)-2-phenyl-1,3-thiazol-5-yl] acetyl] amide} ethanesulfonic acid |

TABLE 1-continued

Preferred Formula (I) Compounds

| R Substituent | Formula (I) Compound |
|---|---|
| 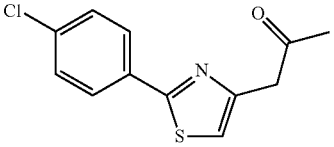<br>derived from 4-[(4-chlorophenyl)-1,3-thiazol-5-yl] acetic acid | 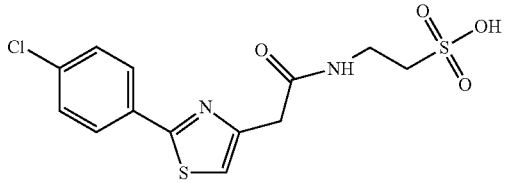<br>Compound 62: 4-{[[(4-chlorophenyl)-1,3-thiazol-5-yl] acetyl] amide} ethanesulfonic acid |
| 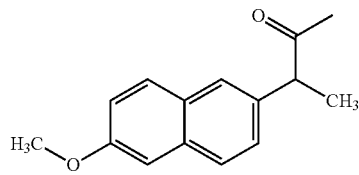<br>derived from 2-(6-methoxy-2-naphthyl) propanoic acid | 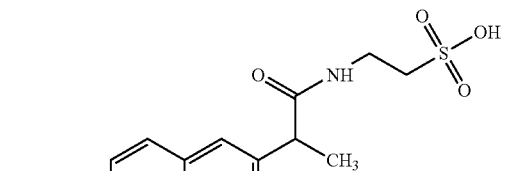<br>Compound 63: 2-{[2-(6-methoxy-2-naphthyl) propanoyl] amide} ethanesulfonic acid |
| 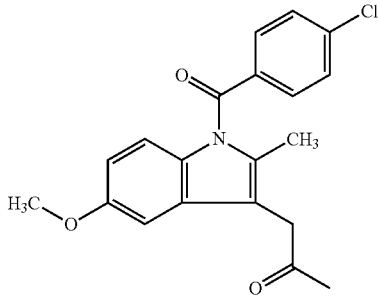<br>derived from [1-(4-chlorobenzoyl)-5-methoxy-2-methyl-1H-indole-3-yl]acetic acid | 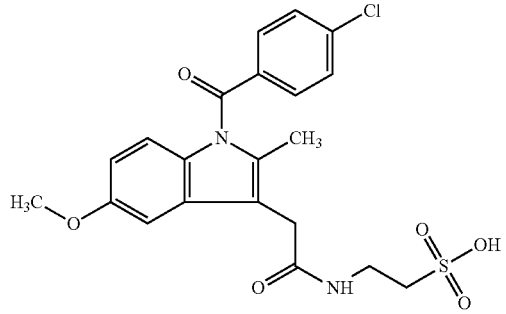<br>Compound 64: [1-(4-chlorobenzoyl)-5-methoxy-2-methyl-1H-indole-3-yl]acetyl]amide} ethanesulfonic acid |
| 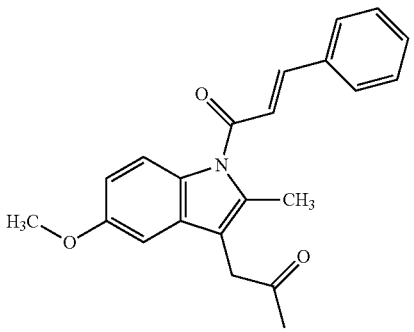<br>derived from {5-methoxy-2-methyl-1-[(2E)-3-phenylprop-2-enoyl]-1H-indole-3-yl} acetic acid | 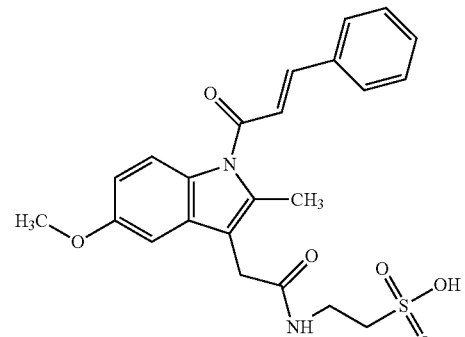<br>Compound 65: {[(5-methoxy-2-methyl-1-[(2E)-3-phenylprop-2-enoyl]-1H-indole-3-yl) acetyl] amide} ethanesulfonic acid |

TABLE 1-continued

Preferred Formula (I) Compounds

| R Substituent | Formula (I) Compound |
|---|---|
| 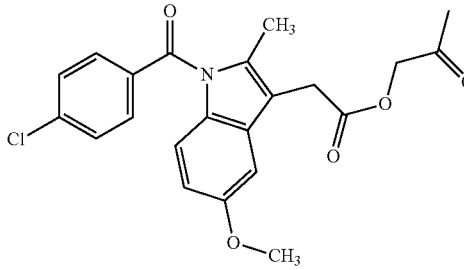<br>derived from ({[1-(4-chlorobenzoyl)-5-methoxy-2-methyl-1H-indole-3-yl]acetyl} oxy) acetic acid | 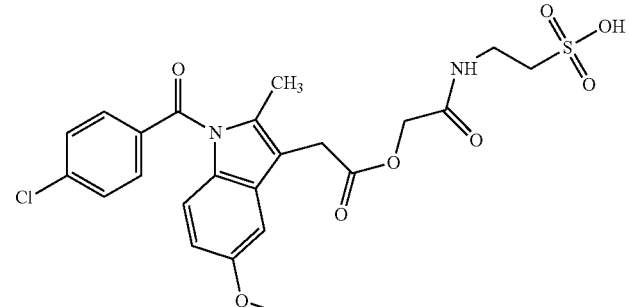<br>Compound 66: {[(5-methoxy-2-methyl-1-[(2E)-3-phenylprop-2-enoyl]-1H-indole-3-yl) acetyl] amide} ethanesulfonic acid |
| 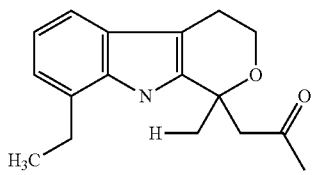<br>derived from (1,8-diethyl-1,3,4,9-tetrahydrofuran[3,4-b]indole-1-yl) acetic acid | 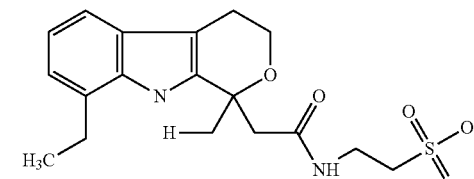<br>Compound 67: {[(1,8-diethyl-1,3,4,9-tetrahydrofuran[3,4-b]indole-1-yl) acetyl] amide} ethanesulfonic acid |
| 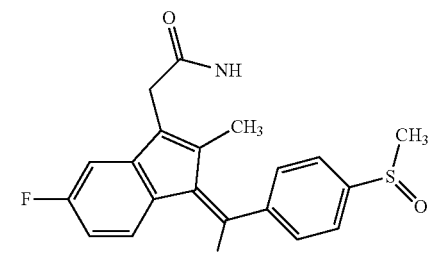<br>derived from {((1E)-5-fluoro-2-methyl-1-[4-(methylsulphony)benzylidene]-1H-inden-3-yl) acetic acid | 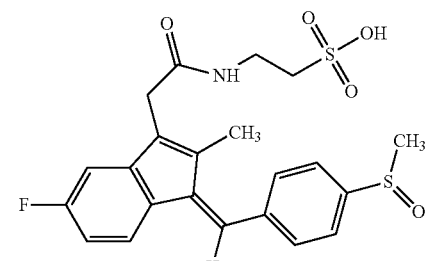<br>Compound 68: {[((1E)-5-fluoro-2-methyl-1-[4-(methylsulphonyl)benzylidene]-1H-inden-3-yl) acetyl] amide} ethanesulfonic acid |
| 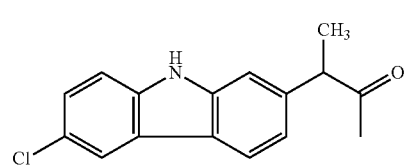<br>derived from 2-(6-chloro-9H-carbazol-2-yl) propanoic acid | 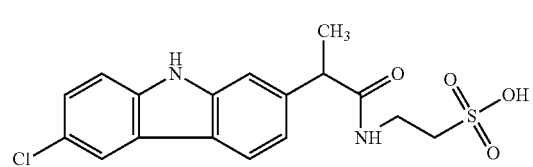<br>Compound 69: 2-{[(6-chloro-9H-carbazol-2-yl) propanoyl] amide} ethanesulfonic acid |

The compounds of the present invention present anti inflammatory activity of the non-steroidal type, antipyretic, analgesic and platelet anti aggregant activity and are useful as adjuvant in the treatment of inflammatory processes such as rheumatoid arthritis, ulcerative colitis, Chron's disease and other inflammatory diseases, such as for example, neurodegenerative diseases such as Alzheimer's disease, with a minimum potential of gastric irritation.

Particularly regarding ulcerative colitis and Chron's disease, the compounds of the present invention provide gastrintestinal anti inflammatory and antioxidant activity.

Taking into consideration that taurine is found in high concentrations in young brains and lowers with the age, and knowing that the inflammatory process is one of the causes of amyloid plate formation in Alzheimer disease, the compounds of the present invention can be useful for the prevention/treatment of this disease, once taurine itself increases the learning capacity in aged animals (El Idrissi, A. Taurine improves learning and retention in aged mice. Neuroscience Letters, 2008 DOI 10.1016/J.neulet 2008.02.070).

The compounds of the present invention are obtained through a process that comprises the reaction of taurine with a substance presenting non-steroidal anti inflammatory (NSAI) activity, in the presence of an appropriate catalyzer, in order to enable the formation of an direct amide bond or by the means an intermediate spacing agent between taurine and the NSAI component.

The substance presenting non-steroidal anti inflammatory activity can be selected from the group consisting of the following NSAI drugs: salycilates, pyrazolons and analogs, derived indoleacetics, derived arilacetics, derived arylpropionics, oxycams and phenamates. The NSAI from the group of salycilates can be chosen from: lysine clonixinate, benorylate, diflunisal, etersalate and salsalate. The NSAI from the group of pyrazolons and analogs can be chosen from: phenylbutazone, oxyphenbutazone, aminophenazone, bumadizone, pheprazone, niphenazone and suxibuzone. The NSAI from the group of the derived indoleacetics can be chosen from: acematacin, glucametacin, indometacin, proglumetacin, oxametacin, sulindac and tolmetin. The NSAI from the group of derived arilacetics can be chosen from: aceclophenac, diclophenac, fentiazac and nabumetone. The NSAI from the group of the derived arylpropionics can be chosen from: butibuphen, phenbuphen, flurbiprophen, ibuprophen, ibuproxam, ketoprophen, naproxen, loxoprofen, panoprofen, oxaprozin and thiaprophen. The NSAI from the group of oxycams can be chosen from: droxicam, meloxicam, pyroxicam and tenoxicam. The NSAI from the group of phenamates can be chosen from: meclophenamic acid, mephenamic acid, tolphenamic acid and niflumic acid.

Preferentially, the process of the present invention for obtaintion of the compounds of the invention is of the latentiation type, in which a chemical modification in a biologically active compound is performed in order to form a novel compound, which will release in vivo the compound or original drug. Latentiation of a drug is synonym of prodrug planning.

However, it is worth noting that mechanism of action of the compounds of the present invention is not completely elucidated and, then, it is not possible to assure that the cited compounds correspond to prodrugs or are novel chemical entities. In other words, the compounds of the present invention can also present activity without the prodrug in vivo breakdown; therefore, it can present activity per se. In fact, when comparing the gastroprotection assays, provided below in the present descriptive report, performed with the compounds of the invention and their physical mixtures with known non-specific and specific NSAIs (for COX-2 inhibition), it was surprisingly observed that the compounds of the present invention did not lead to gastric lesion, have kept the anti inflammatory potency and presented superior safety according to the standards (based on the original NSAIs), as shown in FIGS. 1 to 4.

More precisely, the process of the present invention comprises the reaction of a selected NSAI selected from the anti inflammatory substances as defined herein (original drug) with the ethanesulfonic aminoacid (taurine), in the presence of an appropriate catalyzer, in organic solvent media.

The catalyzer used in the process of the present invention can be any catalyzer used commonly in latentiation processes. It can be cited as preferred ones the following catalyzers: diethylcyanophosphonate, 1-hydroxybenzotriazol, carboiimides, triethyamine, imidazole, pyrazole, 1,2,4-triazole, 4-dimethylaminopyridine, pyridine and similar.

More preferentially, according to the process of the present invention, DEPC (diethylcyanophosphonate).

The process of the present invention is performed, preferentially, in the presence of an organic solvent. The following solvents are preferred: acetone, tetrahydrofuran (THF) or dimethylformamide (DMF).

The reaction can be performed at room temperature, in highly basic media for up to 2 hours. In a preferred way, the precipitated formed is purified by any technique known from the state of technique for obtaining the compound of the invention according to the required specifications by the current legislation for use in the preparation of drugs for human or animal use, such as $C_{15}H_{23}NO_4S$ (embodiment corresponding to Example 1) $C_{16}H_{19}NO_5S$ (embodiment corresponding to Example 2); $C_{21}H_{21}ClN_2O_6S$ (embodiment corresponding to Example 3).

The compounds of the invention are utilizable in the preparation of anti inflammatory drugs in the form of solid, liquid, solid-liquid or solid-gaseous suspensions (for example, aerosols) pharmaceutical compositions, creams, gels, adhesive patches and other pharmaceutical forms of anti inflammatory drugs of systemic use or adequate local application. The preferred pharmaceutical forms are solid, aerosols, creams and gels containing the compounds of the present invention. As solid pharmaceutical forms, it can be cited tablets, capsules, pills and similar. The solid forms can also be of rapid release, controlled or long lasting type. As long as the taurine derived compounds of the present invention are easily soluble, the injectable forms are also preferred, according to the invention.

In the case of injectable forms, the taurine derived compounds of the present invention can be administered by parentheral means, including the endovenous (or intravenous), the muscular, the subepidermal and intradermic. For subepidermal or intravenous administration, the pharmaceutical composition of the invention can be in the form of solution, suspension or emulsion, including substances typically used in such preparations, such as solubilizers, emulsifiers or other additives. The appropriate solvents are water, physiological saline solution or alcohols, for example, ethanol, propanol, glycerol, and, additionally, sugar solutions, such as glucose or mannitol, or mixtures of so called solvents.

The pharmaceutical compositions of the invention can also be in the form of aerosol, such as solutions, suspensions or emulsions of the active ingredient in a pharmaceutically acceptable solvent, such as ethanol or water or their mixtures. It can also be present additives, such as tensoactives, emulsifiers, stabilizers and propellants.

The pharmaceutical compositions of the present invention comprise: (a) at least one of the general formula (I) compounds, (b) optionally, at least one appropriate active principle for the treatment of a medical condition involving an inflammatory disturbance and (c) a pharmaceutically acceptable vehicle or excipient.

The term pharmaceutically acceptable vehicle or excipient with the intention of meaning any substance or substances that are inert used as vehicle or diluents for any of the active principles of the composition of the present invention.

In the case of the pharmaceutical form of the composition of the invention be a tablet, it can include one or more vehicles, excipients and/or additives selected from the group consisting of diluents, desintegrants, ligands, dyes and flavorizant agents. The diluent can be one or more among calcium carbonate, dibasic calcium phosphate, tribasic calcium phosphate, calcium sulphate, microcrystalline cellulose, pulverulent cellulose, dextrats, dextrins, dextrose excipients, fructose, china clay, lactitol, lactose, mannitol, sorbitol, sucrose, compressible sugar and confectioner's sugar, and, in particular, can be lactose. The ligand can be one or more among methylcellulose, hydroxypropylcellulose, hydroxypropyl methylcellulose, polyvinylpyrrolidone, gelatin, gum arabic, ethylcellulose, polyvinylic alcohol, pululane, pre-gelatinized amide, agar, tragacanth, alginic acid-derived and propylene glycol-derived, and alginate, and, in particular, can be polyvinylpyrrolidone. The desintegrant can be one or more among low molecular weight substituted hydroxypropylcellulose, carboxymethyl cellulose, carboxymethyl calcium cellulose, carboxymethyl sodium cellulose, croscarmellose sodium, amide, crystalline cellulose, hydroxypropyl amide, and amide partially pre-gelatinized.

The pharmaceutical compositions of the present invention can be prepared by processes known from the state of the technique.

It has to be understood that the examples and embodiments described herein are solely for illustrative purpose and that various modifications and changes, in the light of themselves, will be suggestive to the specialists in the technique and must be included in the spirit and scope of this description and the scope of the claims that follow it. All the publications, patents and patent applications cited herein are incorporated by reference in their entirety and for all purposes.

The compounds of the invention are preferentially prepared through a latentiation process with the use of a appropriate catalyzer. Following, a general procedure is provided that can be employed for obtaining prodrugs comprising a first component corresponding to a NSAI and a second component corresponding to taurine, in which the first and second components are directly linked or by the means of an spacing agent, through an amidic bond. Therefore, the general proceeding, described as follow, can be used to prepare any one of the 70 preferred compounds of the invention presented in Table 1.

General Procedure for Obtaining Amides (Taurine Derived) According to the Present Invention An acid compound equivalent (NSAI) is solubilized in DMF previously dried out under molecular screen cleaner. Sequentially, an ice bath, 1,2 diethylcyanophosphonate (DEPC) equivalent, 2 taurine equivalent and 11 previously dried out under molecular screen cleaner triethylamine equivalent are added. The reaction is kept for 2 hours shaking at room temperature.

At end of the reaction, the base excess is removed through nitrogen pull-down, and the remaining solvent is eliminated through evaporation at reduced pressure. The obtained residue is added, in small portions, to a saturated aqueous cold NaHCO₃ solution. The formed precipitated is collected by filtration, washed with a small portion of cold water and dried out under phosphorus pentoxide. The obtained dry mass is grinded under THF, with the solid residue being filtrated and dried out.

EXAMPLE 1

[2-(4-isobuthylphenyl)propanoyl]amide ethanesulfonic acid (Compound 27) Synthesis (Compound Derived from Ibuprophen and Taurine)

One gram of ibuprofen is solubilized in DMF previously dried out under molecular screen cleaner. Sequentially, an ice bath, 0.9 mL of diethylcyanophosphonate (DEPC), 1.212 g of taurine and 7.8 mL of previously dried out under molecular screen cleaner triethylamine are added. The reaction is kept for 2 hours shaking at room temperature.

At end of the reaction, the base excess is removed through nitrogen pull-down, and the remaining solvent is eliminated through evaporation at reduced pressure. The obtained residue is added, in small portions, to a saturated aqueous cold NaHCO₃ solution. The formed precipitated is collected by filtration, washed with a small portion of cold water and dried out under phosphorus pentoxide. The obtained dry mass is grinded under THF, with the solid residue being filtrated and dried out and calculated yield of around 90% (analyzed by high performance liquid chromatography—HPLC)

The study of structural confirmation of the purified product led to the result of Table 2.

TABLE 2

Structural characterization of the resulting Compound from the reaction between taurine and ibuprophen (Compound 27)

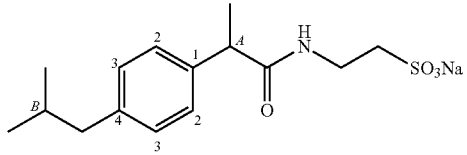

[2-(4-isobuthylphenyl) propanoyl] amide ethanesulfonic acid

| Group | 1H | 13C | HMBC |
|---|---|---|---|
| 1 | — | 135.58 | — |
| 2 | 2H; 7.17 d (J = 8.1 Hz) | 129.42 | 45.45; 127.69; 139.60 |
| 3 | 2H; 7.05 d (J = 8.1 Hz) | 127.69 | 44.70; 45.45; 129.42; 139.60 |
| 4 | — | 139.60 | — |
| —CH— (A) | 1H; 3.46 q (J = 7.1 Hz) | 45.45 | 19.12; 127.69; 139.60; 173.60 |
| —CH— (B) | 1H; 1.79 hep (J = 6.9 Hz) | 30.05 | 22.80; 44.70; 139.60 |
| —CH3 (A) | 3H; 1.28 d (J = 7.1 Hz) | 19.12 | 45.45; 139.60; 173.60 |
| —CH3 (B) | 6H; 0.84 d (J = 6.9 Hz) | 22.80 | 30.05; 44.70 |
| —CH2—Ar | 2H; 2.39 d (J = 7.3) | 44.70 | 22.80; 30.05; 129.42; 139.60 |
| C=O | — | 173.60 | — |
| NH | 1H; 7.81 t (J = 5.3 Hz) | — | 36.60; 173.60 |
| NH—CH2— | 2H; 3.26 | 36.60 | 50.98; 173.60 |
| —CH2—SO3Na | 2H; 2.49 | 50.98 | 36.60 |

EXAMPLE 2

2-{[2-(6-methoxy-2-naphthyl)propanoyl] amide}ethanesulfonic acid (Compound 63) Synthesis One gram of naproxen is solubilized in DMF previously dried out under molecular screen cleaner. Sequentially, an ice bath, 0.8 mL of diethylcyanophosphonate (DEPC), 1.085 g of taurine and 7.0 mL of previously dried out under molecular screen cleaner triethylamine are added. The reaction is kept for 2 hours shaking at room temperature.

At end of the reaction, the base excess is removed through nitrogen pull-down, and the remaining solvent is eliminated through evaporation at reduced pressure. The obtained residue is added, in small portions, to a saturated aqueous cold NaHCO$_3$ solution. The formed precipitated is collected by filtration, washed with a small portion of cold water and dried out under phosphorus pentoxide. The obtained dry mass is grinded under THF, with the solid residue being filtrated and dried out and calculated yield of around 90% (analyzed by HPLC).

After the purification of the product, the study of structural confirmation led to the result of Table 3.

TABLE 3

Structural characterization of the resulting Compound from the reaction between taurine and naproxen (Compound 63)

2-{[2-(6-methoxy-2-naphthyl) propanoyl] amide} ethanesulfonic acid

| Group | 1H | 13C | HMBC |
|---|---|---|---|
| 1 | — | 157.75 | — |
| 2 | 1H; 7.12 dd (J = 9.0 and 1.7 Hz) | 119.1 | 106.46; 129.31; 157.75 |
| 3 | 1H; 7.76 d (J = 9.0 Hz) | 130.23 | 125.88; 129.31; 133.85; 157.75 |
| 4 | 1H; 7.68 sl | 125.88 | 45.8; 127.31; 130.23; 133.85 |
| 5 | — | 138.28 | — |
| 6 | 1H; 7.40 d (J = 8.5 Hz) | 127.31 | 45.8; 106.46; 125.88; 133.85 |
| 7 | 1H; 7.72 d (J = 8.5 Hz) | 128.8 | 129.31; 138.28 |
| 8 | 1H; 7.25 sl | 106.46 | 119.1; 128.8; 157.75 |
| 9 | — | 129.31 | — |
| 10 | — | 133.85 | — |
| CH3—O— | 3H; 3.84 s | 65.36 | 106.46; 157.75; |
| CH3— | 3H; 1.38 d (J = 6.95 Hz) | 18.70 | 45.8; 138.28; 173.70 |
| CH— | 1H; 3.64 q (J = 7.0 Hz) | 45.8 | 18.70; 125.88; 133.85; 138.28; 173.70 |
| C=O | — | 173.70 | — |
| NH | 1H; 7.88 t (J = 5.5 Hz) | — | 36.3; 173.70 |
| NH—CH2— | 2H; 3.26 | 36.3 | 51.05; 173.70 |
| —CH2—SO3Na | 2H; 2.49 | 51.05 | 36.3 |

EXAMPLE 3

[1-(4-chlorobenzoyl)-5-methoxy-2-methyl-1H-indole-3-yl]acetyl]amide}ethanesulfonic acid (Compound 64) Synthesis One gram of indometacin is solubilized in DMF previously dried out under molecular screen cleaner. Sequentially, an ice bath, 0.5 mL of diethylcyanophosphonate (DEPC), 0.700 g of taurine and 4.5 mL of previously dried out under molecular screen cleaner triethylamine are added. The reaction is kept for 2 hours shaking at room temperature.

At end of the reaction, the base excess is removed through nitrogen pull-down, and the remaining solvent is eliminated through evaporation at reduced pressure. The obtained residue is added, in small portions, to a saturated aqueous cold NaHCO$_3$ solution. The formed precipitated is collected by filtration, washed with a small portion of cold water and dried out under phosphorus pentoxide. The obtained dry mass is grinded under THF, with the solid residue being filtrated and dried out and calculated yield of around 90% (analyzed by HPLC).

After the purification of the product, the study of structural confirmation led to the result of Table 4.

TABLE 4

Structural characterization of the resulting Compound from the reaction between taurine and indometacin (Compound 64)

[1-(4-chlorobenzoyl)-5-methoxy-2-methyl-1H-indole-3-yl]acetyl]amide} ethanesulfonic acid

| Group | 1H | 13C | HMBC |
|---|---|---|---|
| 1 | — | 129.5 | — |
| 2 | 2H; 7.75 d (J = 8.2 Hz) | 134.95 | 131.95; 138.23; 168.7 |
| 3 | 2H; 7.62 d (J = 8.2 Hz) | 131.95 | 129.5; 134.95; 138.23; 168.7 |
| 4 | — | 138.23 | — |
| 5 | — | 130.9 | — |
| 6 | 1H; 7.03 d (J = 9.0 Hz) | 119.32 | 101.7; 130.9; 156.32 |
| 7 | 2H; 6.70 dd (J = 9.0 and 2.3 Hz) | 102.16 | 102.16; 130.9; 156.32 |
| 8 | — | 156.32 | — |
| 9 | 1H; 7.06 d (J = 2.3 Hz) | 101.7 | 114.7; 130.9; 156.32 |
| 10 | — | 114.7 | — |
| 11 | — | 129.5 | — |
| 12 | — | 136.1 | — |
| C=O | — | 168.7 | — |
| —CH3 | 3H; 2.15 s | 14.0 | 114.7; 119.32; 136.1; 169.35 |
| —O—CH3 | 3H; 3.76 s | 65.2 | 156.32 |
| —CH2—C=O | 3.48 s * | 55.9 | 114.7; 130.9; 136.1; 169.35 |
| —C=ONH | — | 169.35 | — |
| NH | 1H; 7.88 t (J = 5.2 Hz) | — | 169.35; 35.9 |
| NH—CH2— | 2H; 3.32 t (J = 5.4 Hz) | 35.9 | 169.35 |
| —CH2—SO3Na | 2H; 2.53 t (J = 6.65 Hz) | 51.03 | 35.9 |

EXAMPLE 4

Biological Assay

Since taurine has the ability of inhibiting iNOS present in the macrophages of the inflammatory processes, the objective of this study was of verifying if the binding of the anti inflammatory component of the group of NSAIs to taurine would cause alteration in this activity, in other words, if the capacity of taurine to inhibit iNOS would be reduced, therefore abolishing its anti inflammatory activity.

The assay used the maximum production of nitric oxide (macrophages stimulated with LPS), by indirect method of nitrite ($NO_2^-$) detection as positive control, and in the negative control aminoguanidine, a false enzymatic substrate, was used, leading to the observation of total inhibition of nitric oxide production.

The results have demonstrated that the non-steroidal anti inflammatory (NSAI) drugs do not present NOS inhibition activity, once the NO production was the same as observed in the positive control (LPS).

The results obtained with the use of the compounds of the present invention have demonstrated that they were active in the NO production, similar to taurine, suggesting that the binding of NSAIs to taurine did not modify this activity.

These results suggest that the taurine derived compounds of the present invention can undergo hydrolysis and taurine release during the length of the experiment (24 hours) as well as present activity per se, thus not being prodrugs but analogs (hybrids).

In order to prove that the reduction in the NO production was not caused by cell death, it was performed a test of cellular viability using the compounds of the invention when it was, thus, possible prove the validity of the previous experiment.

This way, it was performed in vivo tests, described below, and, after formation of paw's edema, the following compounds were administered: $C_{16}H_{19}NO_5S$ (example 2); $C_{21}H_{21}ClN_2O_6S$ (example 3); $C_{15}H_{23}NO_4S$ (example 1) that demonstrated to present anti inflammatory activity with dosage of 44 mg/kg; 130 mg/Kg and 182 mg/Kg respectively.

The experiments were performed according equimolar experiments for molecular modification products described by BANDARAGE et al. (BANDARAGE et al. "Nitrosothiol esters of diclofenac: Synthesis and pharmacological characterization as gastrointestinal-sparing prodrugs", Journal of Medicinal Chemistry, v. 43, p. 4005-16, 2000); BANOGLU, et al. (BANOGLU, et al. "Amide derivatives of [6-(5-Methil-3phenylpyrarole-1-yl)-3-(2H)-pyridazinone-2-yl]acetic acids as potential analgesic and anti-inflammatory compounds", Archives of the Pharmacy and Pharmaceutical Medicinal Chemistry, v. 337, p. 7-14, 2004); RANATUNG, et al. (RANATUNG, et al. "Synthesis and anti-inflammatory activity of series of N-substituted naproxen glycolamides: Nitric oxide-donor naproxen prodrugs", Bioorganic and Medicinal Chemistry, v. 14, p. 2589-99, 2006); ÖZTÜRK, G. et al. (ÖZTÜRK, G. et al. "New analgesic and antiinflammatory agents 4(1H)-pyridinone derivatives", Europe Journal Medicinal Chemistry, v. 37, n. 10 p. 829-34, 2002); LOLLI, et al. (LOLLI, et al. "A new class of ibuprofen derivatives with reduced gastrotoxicity", Journal of Medicinal Chemistry, v. 44, p. 3463-68, 2001). Besides these, a paw's edema test was performed using taurine as control of its derived compounds, in the dosage of 10 mg/Kg according to HIRATA, T. et al. (HIRATA, T. et al. "Cyclo-oxygenase isozymes in mucosal ulcergenic and functional responses following barrier disruption in rat stomachs", British Journal of Pharmacology, v. 122, p. 447-54, 1997).

Experimental Outline

In order to confirm the biological activity of the compounds of the present invention, tests were performed according to the pharmacological model of Wistar rat paw's edema using groups of six animals. It was verified that, in the reported concentrations, in the presence of equimolar dosages of the compounds described in the articles above-mentioned, such as referral drugs, a reduction of the inflammatory process with the use of the compounds of the invention was observed.

The compounds of the present invention were administered 1 (one) hour prior the inoculation of the irritant agent carragenin in the paws of the animals, with the aid of a gavage tube, orally, using water as solvent. The following of the inflammation and anti inflammatory activity of the compounds of the invention was performed through measurements of thickness, in millimeters, of the rat's paw.

The control group had the irritant agent carragenin applied to the bottom of their posterior paws and, orally, saline solution. The taurine, the ibuprophen, the naproxen and the indometacin were administered orally to other groups of animals (positive controls), 60 minutes prior to the carragenin (bottom of the paw). Other groups of animals had the taurine derived of the present invention (embodiments corresponding to Examples 1, 2 and 3, respectively—orally) administered 60 minutes prior to the carragenin (bottom of the paw).

The posterior paws were measured prior to the treatments and at each hour, for 6 hours after the carragenin was administered, using an thickness meter, in order to measure their volume (in mm). The results were expressed by the difference between the paw's measurement readings before and after the treatments.

As shown by FIGS. 1-4, 6 hours after the compounds of the invention were administered; they led to statistically equipotent anti inflammatory activity compared to the respective original drugs.

EXAMPLE 5

Acute Toxicity (Single Dosage) (LD50)

The lethal dosage 50 is differentiated depending on the type of NSAI employed. For the ibuprophen derived compound (compound 27), the $LD_{50}$ is of 1,050 mg/Kg; for the naproxen derived compound (compound 63), $LD_{50}$ is of 1,234 mg/Kg (see MERK INDEX, 2006—14° ed.). Based in these data, the experiments about the performance of the compounds of the invention regarding acute toxicity were performed with dosages of 1,000 mg/kg and 1,500 mg/kg.

In the experiments of dosage administration of 1,000 mg/kg of each one of the compounds 27 (synthesis product of taurine with ibuprophen), 63 (synthesis product of taurine with naproxen) and 64 (synthesis product of taurine with indometacin) of the invention (corresponding to the embodiments of the examples 1, 2 and 3) were verified that: (i) in the group that had compound 27 administered, there was no death in any of the tested dosages, presenting values above the ones described for ibuprophen, in oral administration toxicity assay ($LD_{50}$=1,050 mg/Kg); (ii) in the group that had compound 63 administered, in the dosage of 1,000 mg/Kg, all animals survived, and in the dosage of 1,500 mg/Kg there was only 17% of deaths, which is superior to the data found in the literature for the naproxen ($LD_{50}$=1,234 mg/Kg); and in the group that had compound 64 administered, in the dosage of 1,000 mg/Kg, no animal has died and in the dosage of 1,500 mg/Kg, 66% of the population survived to the toxicity assay.

Experimental Outline

Wistar female rats weighting between 200 and 250 g were used. The control group had only saline solution administered. To all studied groups, dosages of 1,000 and, alternatively, of 1,500 mg/kg were administered by gavage feeding.

After fourteen (14) days of administration and observation regarding the toxicity signs of general kind, effects on motion, behavior, breathing, number of deaths and form of occurrence, the animals that have survived were subjected to euthanasia in $CO_2$ and had their organs such as heart, lungs, kidney, liver and stomach removed and weighted. For the analysis of the results were also considered the body weights.

The difference of the weight of the organs (kidney, heart and liver) of the tested animals for the three compounds of the invention is shown in FIGS. 4 to 9, being possible to observe that the results, regarding weight, with the administration of the compounds 28, 64 and of the invention are substantially close of those obtained with the control animals.

EXAMPLE 6

Gastric Ulcerogenesis

Gastric ulcerogenesis was verified in the same animals of the groups used for the model of paw's edema.

After 6 hours of the paw's measurement readings, the animals were subjected to euthanasia in $CO_2$, and had their stomach removed, cut open in the longitudinal axis and washed with saline solution. In all experiments, the groups were composed of 6 animals, being kept the desired therapeutic activity, with absence of gastric lesions, and after the $LD_{50}$ assays, it was concluded that the taurine derived compounds of the present invention are safe. It is worth observing, still, that other organs, such as lungs and intestine, as well as the macroscopic integrity of the other organs were kept preserved.

Experimental Outline

Figure 10:
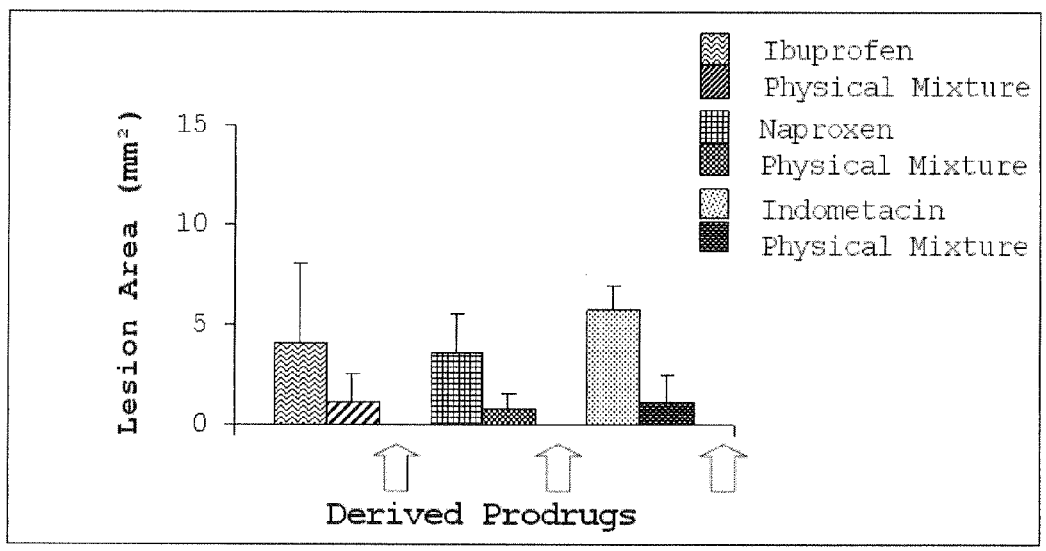
FIG. 10 graphically shows the gastrotoxicity tests that have been conducted: (i) with the NSAI drugs ibuprophen, naproxen and indometacin, with the equimolar physical mixture of taurine with these NSAI drugs and (iii) with the compounds 63 (taurine-ibuprophen), 27 (taurine-naproxen) and 64 (taurine-indometacin) of the invention.

Through mucous membrane exposition, it was observed its color and integrity. In the case of lesions existence, they were counted and measured, according to the gastric ulcerogenesis index (G.U.I.) that follows numeric criteria for classification of lesions of the gastric mucous membrane: (lesions<1 mm=1; 1.5 to 2.5 mm=2; 2.5 to 3.5 mm=3; 3.5 to 4.5 mm=4 and >4.5 mm=5). The obtained results were reported as averages±E. P. M. The results of the lesion experiment regarding the administration of the compounds of the present invention (embodiments corresponding to the Examples 1, 2 and 3) were neither macroscopically nor microscopically (640×) observed, being reported as lesion index of 0 (zero) value. Additionally, with the administration of these compounds of the invention, it was not observed alterations in the mucous membrane. FIG. 10 shows this surprising result of no gastric lesion in the anti inflammatory activity of the compounds of the invention.

All NSAI compounds presented a maximum lesion index, with stipulated value of 5 (five), forming lesions with hemorrhagic spots. It is worth observing that, for the group of animals of ibuprophen administration, their stomachs presented color alteration of the mucous membrane, as opposed to its correspondent derived compound (compound 27), which did not present any color alteration in the mucous membrane, keeping its integrity.

In all associations, the reduction of the lesion area was accompanied by the non alteration of the gastric mucous membrane or of hemorrhagic spots.

With no intentions of explaining the reason of the excellent results of the molecular modifications in anti inflammatory drugs with the introduction of transporter as obtained by the compounds of the present invention, the advantages presented by these can be attributed, regarding the ulcerogenesis tests, to the differential and perfected release profile or per se activity as shown in FIG. 10.

Figure 2:
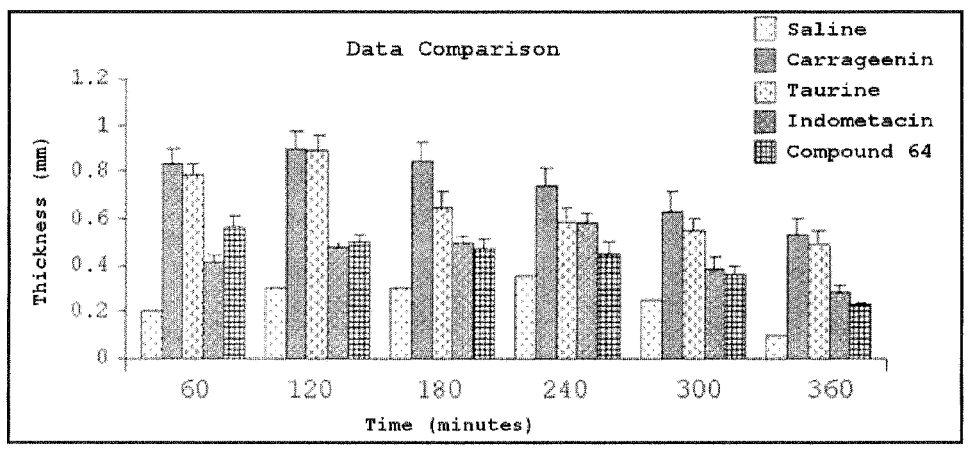
FIG. 2 shows a comparative assay of the anti inflammatory activity per rat's paw using taurine, indometacin and its derived compound (Compound 64, embodiment of the invention corresponding to Example 3).
Figure 3:
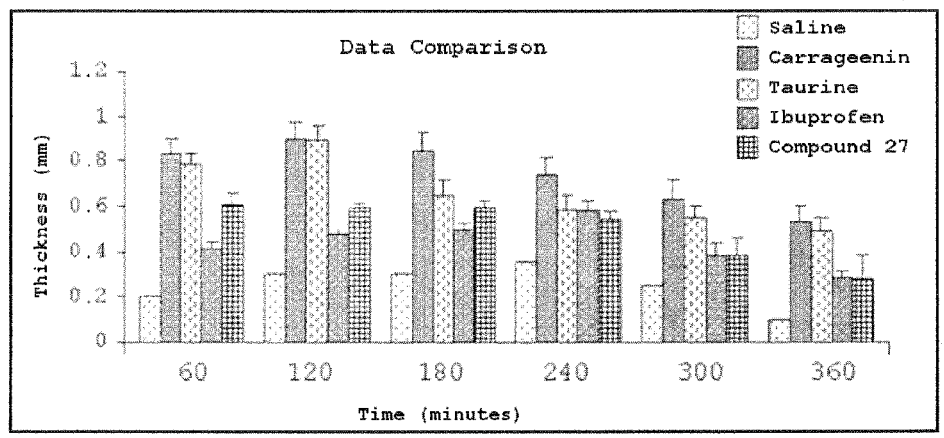
FIG. 3 shows a comparative assay of the anti inflammatory activity per rat's paw using taurine, ibuprophen and its derived compound (Compound 27, embodiment of the invention corresponding to Example 1).
Figure 4:
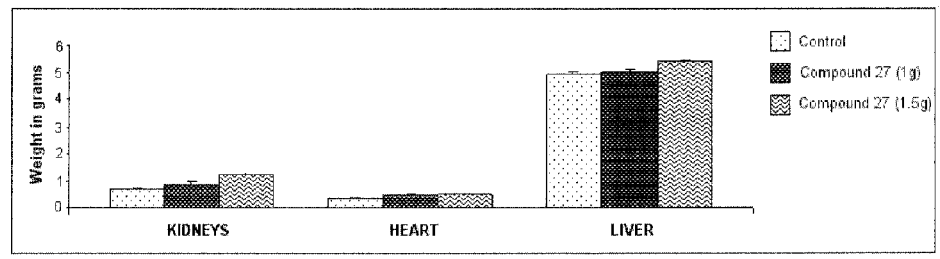
FIG. 4 graphically demonstrates the weight profile, in grams, of the organs: kidneys, heart and liver regarding the body weight of each animal, given in percentage, when the ibuprophen-derived compound is administered after the toxicity assay (Compound 27, embodiment of the invention corresponding to Example 1).
Figure 5:
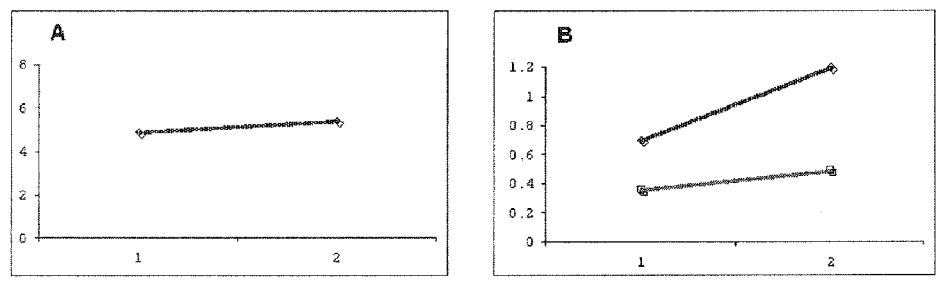
FIG. 5 graphically shows the organ weight differences when the ibuprophen-derived compound is administered: In A=liver; and B, the superior slope equals to kidneys and the inferior one to the heart.
Figure 6:
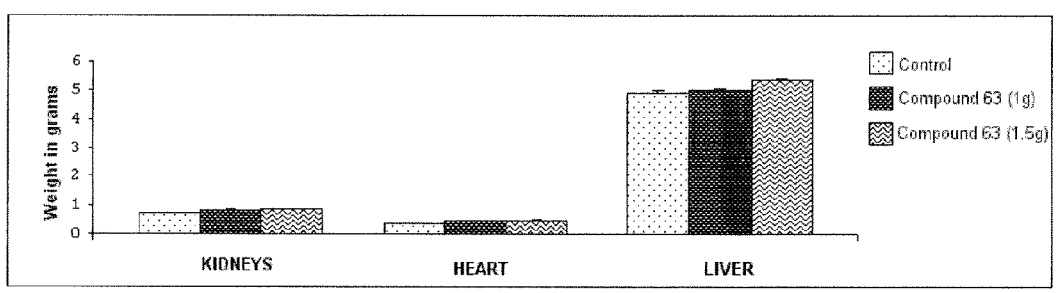
FIG. 6 graphically represents the weight profile, in grams, of the organs: kidneys, heart and liver related to the body weight of each animal, given in percentage, when the naproxen-derived is administered after the toxicity assay (Compound 63, embodiment of the invention corresponding to Example 2).
Figure 7:
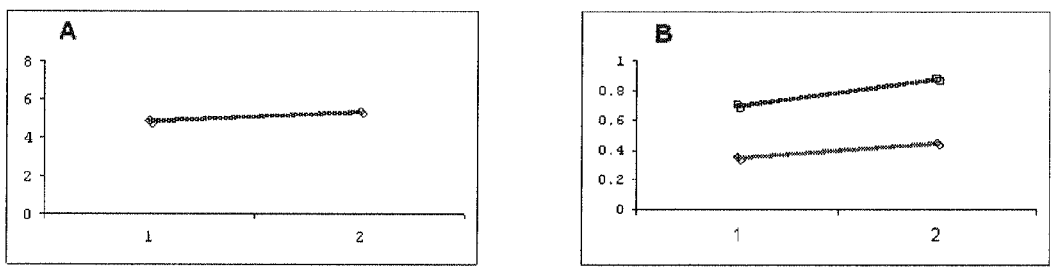
FIG. 7 graphically shows the organ weight differences when the naproxen-derived compound is administered: In A=liver; and B, the superior slope equals to kidneys and the inferior one to the heart.
Figure 8:
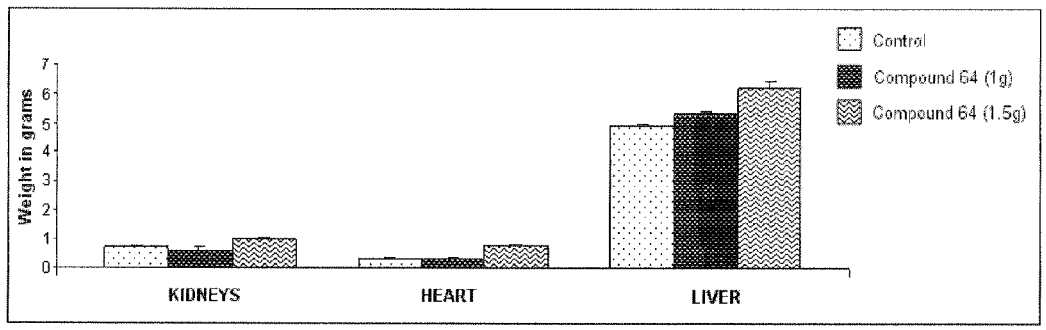
FIG. 8 graphically represents the weight profile, in grams, of the organs: kidneys, heart and liver related to the body weight of each animal, given in percentage, when the indometacin-derived is administered after the toxicity assay (Compound 64, embodiment of the invention corresponding to Example 3).
Figure 9:
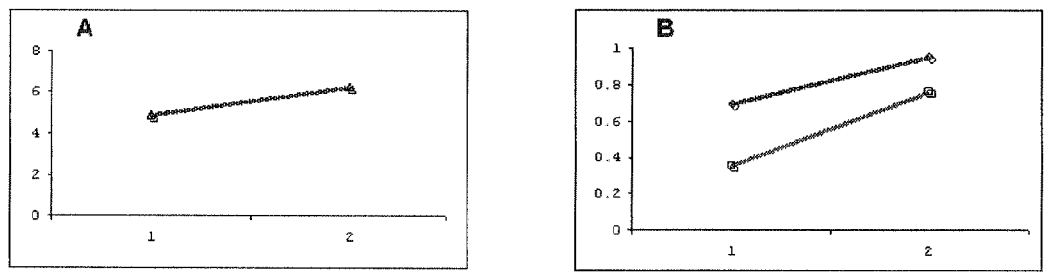
FIG. 9 graphically shows the organ weight differences when the indometacin-derived compound is administered: In A=liver; and B, the superior slope equals to kidneys and the inferior one to the heart.

It is interesting to observe that, in the first hour of the experiment, in the paw's edema test, the anti inflammatory activity of the compounds of the invention have presented itself as inferior in comparison to the one of the original drugs, but this pattern was totally reversed as shown in FIGS. 1-3.

Although the meaning of these results cannot be limited to a theoretical explanation, it can be said that the latentiation process would explain this behavior of the compounds of the present invention, that is, moderate activity in the beginning (after administration), with the obtaintion of inferior values of anti inflammatory activity and, in the end, responses similar to the respective original drugs, with the advantage to the drastic reduction of the gastric lesions. However, as seen for aspirin, they could also present activity as structural analogs and including their metabolites.

All of the results were submitted to the variance homogeneity (Levene's test to certify homogeneity). The results with non-significant p (above 0.05) were further submitted to Analysis of Variance (ANOVA), followed by the multiple comparisons test (post hoc analysis) as the Newman-Keuls' test; and it was only considered the values of p when they were equal or inferior to 0.05.

All of the publications and patent applications mentioned in the description are indicatives of the level of those specialists in the technique to which the invention relates to. All the publications and patent applications are incorporated herein by references to the same extent as if each individual publication or each patent application were specifically and individually indicated to be incorporated by reference.

Even though the precedent invention has been described in some details by means of illustration and examples for clarity and understanding purposes, it will be obvious that certain changes and modifications can be performed within the scope of the claims that accompanies this description.

That which is claimed:
1. A taurine derivative compound of Formula (I)

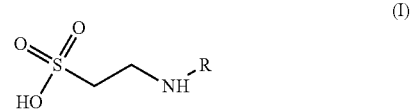

and its salts, solvates, hydrates, enantiomers, diasteroisomers and polymorphs:
in which R is derived and selected from the group of compound consisting of:
2-[(2,6-dichloro-3-methylphenyl)amino]benzoic acid,
2-{[3-(trifluoromethyl)phenyl]amino}nicotinic acid,
2-[(2,3-dimethylphenyl)amino]benzoic acid,
[2-(2,4-dichlorophenoxy)phenyl]acetic acid,
2-[(3-chloro-2-methylphenyl)amino]benzoic acid,
2-[(1,2-diphenyl-hydrazine)carbonyl]hexanoic acid,
4-[(4-butyl-3,5-dioxo-1,2-diphenylpyrazolidin-4-yl)methoxy]-4-oxobutanoic acid,
(1,3,4-triphenyl-1H-pyrazol-5-yl)acetic acid,
[3-(4-chlorophenyl)-1-phenyl-1H-pyrazol-4-yl]acetic acid,
[(1-benzyl-1H-indazole-3-yl)oxy]acetic acid,
[2-(4-chlorophenyl)-1,3-thiazol-4-yl]acetic acid,
3-(4,5-diphenyl-1,3-oxazol-2-yl)propanoic acid,
2-amino-6-benzyl-4,5,6,7-tetrahydrothien[2,3-c]pyridine-3-carboxylic acid,
2-(2-hydroxybenzoylic)acid,
[2-(aminocarbonyl)phenoxy]acetic acid,
2,5-dihydroxybenzoic acid,
2-(acetyloxy)benzoic acid,
2-(sulphooxy)benzoic acid,
2-[(2-hydroxybenzoyl)oxy]benzoic acid,
2-[(2-phenylethyl)amino]benzoic acid, 5-[(2-phenyl-4,5-dihydro-3H-benzo[e]-1H-indole-2-(2-hydroxybenzoic acid),
2',4'-difluoro-4-hydroxy-1,1'-diphenyl-3-carboxylic acid,
2-(3-phenoxyphenyl)propanoic acid,
chloro(3-chloro-4-cyclo-hexylphenyl)acetic acid,
4-(3-chloro-4-cyclo-hexylphenyl)-4-oxobutanic acid,
6-chloro-5-cyclo-hexylindan-1-carboxylic acid,
2-{4-[(2-methylprop-2-enyl)amino]phenyl}propanoic acid,
2-(5-benzoyithien-2-yl)propanoic acid,
5-benzoyl-2,3-dihydro-1H-pyrolizine-1-carboxylic acid,
2-[2-(4-fluorophenyl)-1,3-benzoxazol-5-yl]propanoic acid,
2-[2-(4-chlorophenyl)-1,3-benzoxazol-5-yl]propanoic acid,
2-(4-imidazo[1,2-a]pyridin-2-ylphenyl)propanoic acid,
2-[3-chloro-4-(2,5-dihydro-1H-pyrol-1-yl)phenyl]propanoic acid,
carboxylic acid,
(11-oxo-6,11-dihydrodibenzo[b,e]oxepin-2-yl)acetic acid,
[4-(allyloxy)-3-chlorophenyl]acetic acid,
2-[4-(1-oxo-1,3-dihydro-2H-isoindole-2-yl)phenyl]propanoic acid,
6-chloro-5-cyclo-hexylindane-1-carboxylic acid,
2-[4-(2,5-dihydrothien-2-yl carbonyl)phenyl]propanoic acid,
2-(benzoylthien-2-yl)propanoic acid,
[1-(4-chlorophenyl)-2,5-dimethyl-1H-pyrol-3-yl]acetic acid,
2-(5H-cromeno[2,3-b]pyridin-7-yl)propanoic acid,
4-(1,1'-diphenyl-4-yl)-4-oxobutanic acid,
[4-(4-chlorophenyl)-1,3-thiazol-5-yl]acetic acid,
2-(6-methoxy-2-naphthyl)propanoic acid,
[1-(4-chlorobenzoyl)-5-methoxy-2-methyl-1H-indole-3-yl]acetic acid,
{5-methoxy-2-methyl-1-[(2E)-3-phenylprop-2-enoyl]-1H-indole-3-yl}acetic acid,
({1-(4-chlorobenzoyl)-5-methoxy-2-methyl-1H-indole-3-yl]acetyl}oxy)acetic acid,
(1,8-diethyl-1,3,4,9-tetrahydrofurane[3,4-b]indole-1-yl)acetic acid,
{(1E-5-fluoro-2-methyl-1-[4-(methylsulphonyl)benzylidene]-1H-inden-3-yl}acetic acid, and
2-(6-chloro-9H-carbazol-2-yl)propanoic acid.

2. The compound according to claim 1, wherein the compound is selected from group consisting of:
2-{[(2,6-dichloro-3-methylpheny)aminobenzoil]amide}ethanesulfonic acid
2-{[3-(trifluoromethyl)phenyl]amino}nicotinoyl]amide}ethanesulfonic acid
2-{[(2,3-dimethylphenyl)amino]benzoyl]amide}ethanesulfonic acid
2-{[(2,4-dichlorophenoxy)phenyl]acetyl]amide}ethanesulfonic acid
2-{[(3-chloro-2-methylphenyl)amino]benzoyl]amide}ethanesulfonic acid
2-{[(1,2-diphenyl-hydrazino)carbonyl]hexanoyl]amide}ethanesulfonic acid
4-{[(4-butyl-3,5-dioxo-1,2-diphenylpyrazolidin-4-yl)methoxy]-4-oxobutanoyl]amide}ethanesulfonic acid
{[(1,3,4-triphenyl-1H-pyrazol-5-yl)acetyl]amide}ethanesulfonic acid
{[[3-(4-chlorophenyl)-1-phenyl-1H-pyrazol-4-yl]acetyl]amide}ethanesulfonic acid
{[(1-benzyl-1H-indazol-3-yl)oxy]acetyl]amide}ethanesulfonic acid
{[[2-(4-chlorophenyl)-1,3-thiazol-4-yl]acetyl]amide}ethanesulfonic acid
3-{[(4,5-diphenyl-1,3-oxazol-2-yl)propanoyl]amide}ethanesulfonic acid
2-{[amino-6-benzyl-4,5,6,7-tetrahydrothieno[2,3-c]pyridine-3-carboxylyl]amide}ethanesulfonic acid
{[[2-(aminocarbonyl)phenoxy]acetyl]amide}ethanesulfonic acid
[(2,5-dihydroxybenzoyl)amide]ethanesulfonic acid
{[2-(sulphooxy)benzoyl]amide}ethanesulfonic acid
2-{[(2-hydroxybenzoyl)oxy]benzoyl]amide}ethanesulfonic acid
2-{[(2-phenylethy)amino]benzoyl]amide}ethanesulfonic acid
5-{[(2-phenyl-4,5-dihydro-3H-benzo[e]-1H-indole-2-(2-hydroxybenzoyl)amide]}ethanesulfonic acid
[(2',4'-difluoro-4-hydroxy-1,1'-diphenyl-3-carboxylyl)amide]ethanesulfonic acid
{2-(3-phenoxyphenyl)propanoyl}amide ethanesulfonic acid
[chloro (3-chloro-4-cyclo-hexylphenyl)acetyl]amide ethanesulfonic acid
[4-(3-chloro-4-cyclo-hexylphenyl)-4-oxobutanoyl]amide ethanesulfonic acid
(6-chloro-5-cyclo-hexylindane-1-carboxyl)amide ethanesulfonic acid
2-{4-[(2-methylprop-2-enil)amino]phenyl-propanoyl}amide ethanesulfonic acid
[2-(5-benzoylthien-2-yl)propanoyl]amide ethanesulfonic acid
(5-benzoyl-2,3-dihydro-1H-pyrolizine-1-carboxyl)amide ethanesulfonic acid
{2-[2-(4-fluorophenyl)-1,3-benzoxazol-5-yl]propanoyl}amide ethanesulfonic acid
{2-[2-(4-chlorophenyl)-1,3-benzoxazol-5-yl]propanoyl}amide ethanesulfonic acid
[2-(4-imidazo[1,2-a]pyridin-2-ylphenyl)propanoyl]amide ethanesulfonic acid
[2-(5-benzoylthien-2-yl)propanoyl]amide ethanesulfonic acid
{2-[3-chloro-4-(2,5-dihydro-1H-pyrol-1-yl)phenyl]propanoyl}amide ethanesulfonic acid
[(11-oxo-6,11-dihydrodibenzo[b,e]oxepin-2-yl)acetyl] amide ethanesulfonic acid
{[4-(allyloxy)-3-chlorophenyl]acetyl}amide ethanesulfonic acid
{2-[4-(1-oxo-1,3-dihydro-2H-isoindole-2-yl)phenyl]propanoyl}amide ethanesulfonic acid
{2-[4-(2,5-dihydrothien-2-ylcarbonyl)phenyl]propanoyl}amide ethanesulfonic acid
[2-(5-benzoylthien-2-yl)propanoyl]amide ethanesulfonic acid
2-{[(5H-chromene[2,3-b]pyridin-7-yl)propanoyl]amide}ethanesulfonic acid
4-{[(1,1'-biphenyl-4-yl)-4-oxobutanoyl]amide}ethanesulfonic acid
2-{[2-(6-methoxy-2-naphthyl)propanoyl]amide}ethanesulfonic acid
[1-(4-chlorobenzoyl)-5-methoxy-2-methyl-1H-indole-3-yl]acetyl]amide}ethanesulfonic acid
{[(5-methoxy-2-methyl-1-[(2E)-3-phenylprop-2-enoyl]-1H-indole-3-yl)acetyl]amide}ethanesulfonic acid
{[(1,8-diethyl-1,3,4,9-tetrahydrofuran[3,4-b]indole-1-yl)acetyl]amide}ethanesulfonic acid
{[((1E)-5-fluoro-2-methyl-1-[4-(methylsulphonyl)benzylidene]-1H-inden-3-yl)acetyl]amide}ethanesulfonic acid 2-{[(6-chloro-9H-carbazol-2-yl)propanoyl]
  amide}ethanesulfonic acid.

3. The compound according to claim 1, wherein the compound is selected from the group consisting of:

2-{[2-(6-methoxy-2-naphthyl)propanoyl]
  amide}ethanesulfonic acid; and

[1-(4-chlorobenzoyl)-5-metoxy-2-methyl-1H-indole-3-
  yl]acetyl]amide}ethanesulfonic acid.

\* \* \* \* \*